US008889964B1

(12) United States Patent
Clark et al.

(10) Patent No.: US 8,889,964 B1
(45) Date of Patent: *Nov. 18, 2014

(54) POTATO CULTIVAR W8

(71) Applicant: J.R. Simplot Company, Boise, ID (US)

(72) Inventors: Pete Clark, Eagle, ID (US); Susan Fortier Collinge, Eagle, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,415

(22) Filed: Jun. 17, 2014

(51) Int. Cl.
*A01H 5/00* (2006.01)
*C12N 15/82* (2006.01)
*A23L 1/216* (2006.01)

(52) U.S. Cl.
CPC ............ *C12N 15/8282* (2013.01); *A23L 1/216* (2013.01); *C12N 15/8275* (2013.01); *C12N 15/8247* (2013.01); *C12N 15/8283* (2013.01); *C12N 15/8281* (2013.01); *C12N 15/8245* (2013.01); *C12N 15/8289* (2013.01); *C12N 15/8274* (2013.01); *C12N 15/8278* (2013.01); *C12N 15/8286* (2013.01); *C12N 15/8251* (2013.01)
USPC ........ 800/317.2; 800/295; 800/298; 800/260; 800/263; 800/266; 800/268; 800/278; 800/284; 800/285; 800/286; 435/419

(58) Field of Classification Search
None
See application file for complete search history.

(56) References Cited

U.S. PATENT DOCUMENTS

| | | | |
|---|---|---|---|
| 6,160,204 A | 12/2000 | Steffens | |
| 7,250,554 B2 | 7/2007 | Rommens et al. | |
| 7,534,934 B2 | 5/2009 | Rommens et al. | |
| 7,619,138 B2 | 11/2009 | Rommens et al. | |
| 7,713,735 B2 | 5/2010 | Rommens et al. | |
| 7,880,057 B2 | 2/2011 | Rommens et al. | |
| 7,947,868 B2 | 5/2011 | Rommens et al. | |
| 8,143,477 B2 | 3/2012 | Rommens | |
| 8,158,414 B2 | 4/2012 | Rommens et al. | |
| 8,193,412 B2 | 6/2012 | Rommens et al. | |
| 8,252,974 B2 | 8/2012 | Rommens | |
| 8,273,949 B2 | 9/2012 | Rommens et al. | |
| 8,502,027 B2 | 8/2013 | Rommens | |
| 8,674,177 B2 | 3/2014 | Rommens et al. | |
| 8,710,311 B1 | 4/2014 | Clark et al. | |
| 8,754,303 B1 | 6/2014 | Clark et al. | |

FOREIGN PATENT DOCUMENTS

| | | | |
|---|---|---|---|
| WO | WO 94/03607 A1 | 2/1994 | |
| WO | WO 2004/040999 | 5/2004 | |

OTHER PUBLICATIONS

Rommens et al. Low-acrylamide french fries and potato chips. (2008) Plant Biotechnology Journal; vol. 6, pp. 843-853.*
Coetzer et al. Control of enzymatic browning in potato (*Solanum tuberosum* L.) by sense and antisense RNA from tomato polyphenol oxidase. (2001) J. Agric. Food Chem.; vol. 49, pp. 652-657.*
Sonnewald et al. A second L-type isozyme of potato glucan phosphorylase: cloning, antisense inhibition and expression analysis. (1995) Plant Molecular Biology; vol. 27, pp. 567-576.*
Ritte et al. The starch-related R1 protein is an a-glucan, water dikinase. (2002) PNAS; vol. 99, pp. 7166-7171.*
U.S. Appl. No. 14/264,265, filed Apr. 29, 2014, Clark, et al.
U.S. Appl. No. 14/072,487, filed Nov. 5, 2013, Clark, et al.
Coetzer et al., 2001, Control of enzymatic browning in potato (*Solanum tuberosum* L.) by sense and antisense RNA from tomato polyphenol oxidase, J. Agric. Food Chem., 49:652-657.
Richael, et al., 2008, Cytokinin vectors mediate marker-free and backbone-free plant transformation, Transgenic Res, 17:905-917.
Richael, et al., 2012, Employment of cytokinin vectors for marker-free and backbone-free transformation, Methods Mol Biol, 847:3-10.
Ritte et al., 2002, The starch-related R1 protein is an a-glucan, water dikinase, PNAS, 99:7166-7171.
Rommens, C.M., 2004, All-native DNA transformation: a new approach to plant genetic engineering, Trends in Plant Science, 9(9):457-464.
Rommens, et al., 2005, Plant-derived transfer DNAs, Plant Physiology, 139:1338-1349.
Rommens, et al., 2006, Improving potato storage and processing characteristics through all-native DNA transformation, J Agric Food Chem, 54(26):9882-7.
Rommens, C.M., 2007, Intragenic crop improvement: combining the benefits of traditional breeding and genetic engineering, J Agric Food Chem, 55(11):4281-8.
Rommens, et al., 2007, The intragenic approach as a new extension to traditional plant breeding, Trends in Plant Science, 12(9):397-403.
Rommens, et al., 2008, Low-acrylamide French fries and potato chips, Plant Biotechnology Journal, 6:843-853.

(Continued)

*Primary Examiner* — Cathy Kingdon Worley
(74) *Attorney, Agent, or Firm* — Jondle & Associates, P.C.

(57) ABSTRACT

A potato cultivar designated W8 is disclosed. The invention relates to the tubers of potato cultivar W8, to the seeds of potato cultivar W8, to the plants of potato W8, to the plant parts of potato cultivar W8, to food products produced from potato cultivar W8, and to methods for producing a potato plant produced by crossing potato cultivar W8 with itself or with another potato variety. The invention also relates to methods for producing a potato plant containing in its genetic material one or more transgenes and to the transgenic potato plants and plant parts produced by those methods. This invention also relates to potato cultivars or breeding cultivars and plant parts derived from potato variety W8, to methods for producing other potato cultivars, lines or plant parts derived from potato cultivar W8 and to the potato plants, varieties, and their parts derived from use of those methods. The invention further relates to hybrid potato tubers, seeds, plants and plant parts produced by crossing potato cultivar W8 with another potato cultivar.

23 Claims, 10 Drawing Sheets

(56) References Cited

OTHER PUBLICATIONS

Rommens, C.M., 2010, Chapter 4: Precise breeding through all-native DNA transformation in Genetic Modification of Plants, Biotechnology in Agriculture and Forestry 64, F. Kempken and C. Jung (eds), Springer-Verlag, Berlin Heidelberg.

Rommens, et al., 2010, Tastier and healthier alternatives to French fries, J Food Sci, 75(4):H109-15.

Rommens, et al., 2010, Intragenic vectors and marker-free transformation: Tools for a greener biotechnology, in Plant Transformation Technologies (eds C.N. Stewart, A. Touraev, V. Citovsky and T. Tzfira), Wiley-Blackwell, Oxford, UK.

Sonnewald et al., 1995, A second L-type isozyme of potato glucan phosphorylase: cloning, antisense inhibition and expression analysis, Plant Molecular Biology, 27:567-576.

Yan, et al., 2006, New construct approaches for efficient gene silencing in plants, Plant Physiology, 141:1508-1518.

Ye, et al, 2010, Tuber-specific silencing of the acid invertase gene substantially lowers the acrylamide-forming potential of potato, J Agric Food Chem, 58(23):12162-12167.

* cited by examiner

POTATO CULTIVAR W8

BACKGROUND OF THE INVENTION

The present invention relates to a novel potato cultivar designated W8 and to the tubers, plants, plant parts, tissue culture and seeds produced by that potato variety. The invention further relates to food products produced from potato cultivar W8, such as French fries, potato chips, dehydrated potato material, potato flakes and potato granules. All publications cited in this application are herein incorporated by reference.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

The quality of potatoes in the food industry is adversely affected by two critical factors: (1) potatoes contain large amounts of asparagine, a non-essential free amino acid that is rapidly oxidized to form acrylamide, a carcinogenic product, upon frying or baking; and (2) potatoes are highly susceptible to enzymatic browning and discoloration, an undesirable event which happens when polyphenol oxidase leaks out from the damaged plastids of bruised potatoes. In the cytoplasm, the enzyme oxidizes phenols, which then rapidly polymerize to produce dark pigments. Tubers contain large amounts of phosphorylated starch, some of which is degraded during storage to produce glucose and fructose. These reducing sugars react with amino acids to form Maillard products including acrylamide when heated at temperatures above 120° C. Two enzymes involved in starch phosphorylation are water dikinase R1 and phosphorylase-L (R1 and PhL). Browning is also triggered non-enzymatically as a consequence of the partial degradation of starch into glucose and fructose.

Many potato cultivars are susceptible to late blight, a devastating disease caused by the fungus-like oomycete pathogen *Phytophthora infestans*. Late blight of potato is identified by black/brown lesions on leaves and stems that may expand rapidly and become necrotic. Severe late blight epidemics occur when *P. infestans* grows and reproduces rapidly on the host crop.

To date, there are no potato plant varieties that produce tubers with low acrylamide content, increased black spot bruise tolerance, lowered reducing sugars, and increased resistance to late blight. Thus, there is a need to develop potato varieties with reduced levels of toxic compounds and increased resistance to disease, but without the use of unknown or foreign nucleic acids. The present invention satisfies this need.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

To this end, the present invention provides novel potato variety W8 transformed with nucleic acid sequences that are native to the potato plant genome and does not contain foreign DNA, *Agrobacterium* DNA, viral markers or vector backbone sequences. Rather, the DNA inserted into the genome of the potato variety W8 is a non-coding polynucleotide native to potato or native to wild potato, a potato sexually-compatible plant, that silences genes involved in the expression of black spot bruises, asparagine accumulation and senescence sweetening.

Thus, in one embodiment, the present invention provides a plant vector, referred to as pSIM1278, that comprises a first silencing cassette containing two copies of a DNA segment comprising, in anti-sense orientation, a fragment of the asparagine synthetase-1 gene (fAsn1) and the 3'-untranslated sequence of the polyphenol oxidase-5 gene; and a second silencing cassette containing two copies of a DNA segment comprising, in anti-sense orientation, a fragment of the potato phosphorylase-L (pPhL) gene and a fragment of the potato R1 gene. The pSIM1278 vector comprises a 9,512 bp backbone region that supports maintenance of the plant DNA prior to plant transformation and is not transferred into plant cells upon transformation of the plant cells, and a 10,148 bp DNA insert region comprising native DNA that is stably integrated into the genome of the plant cells upon transformation.

In another embodiment, the present invention provides a second plant vector, referred to as pSIM1678, which comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. The pSIM1678 vector comprises a 9,512 bp backbone region that supports maintenance of the plant DNA prior to plant transformation and is not transferred into plant cells upon transformation of the plant cells, and a 9,090 bp DNA insert region comprising native DNA that is stably integrated into the genome of the plant cells upon transformation.

In a different embodiment, the invention provides a plant cell transformed with one or both of the plant vectors of the invention. In a further embodiment, the invention provides a potato plant variety comprising one or more cells transformed with the vectors of the invention. In one aspect of the invention, the potato plant variety expresses at least one of the two silencing cassettes of the vector pSIM1278 and expresses the silencing cassette of the vector pSIM1678, and expression of the silencing cassettes results in the down-regulation of the asparagine synthetase-1 gene, the polyphenol oxidase-5 gene and the vacuolar invertase gene in the tubers of the plant. In a preferred aspect of the invention, the tubers of the potato plant variety expressing at least one silencing cassette display two or more desirable traits that are not present in the tubers of untransformed plants of the same variety. In the most preferred aspect of the invention, the two or more desirable traits are selected from the group consisting of low asparagine accumulation, reduced black-spot bruising, reduced heat-induced acrylamide formation and reduced accumulation of reducing sugars during storage.

In a different aspect of the invention, the potato plant variety expresses both silencing cassettes of the plant DNA vector pSIM1278, and expresses the silencing cassette of the vector pSIM1678, and expression of the silencing cassettes results in the down-regulation of the asparagine synthetase-1 gene, the polyphenol oxidase-5 gene, the phosphorylase-L gene, the dikinase R1 gene and the vacuolar invertase gene in the tubers of the potato plant variety. In a preferred aspect of the invention, the tubers of the potato plant variety expressing two silencing cassettes of the plant DNA vector pSIM1278 and expressing the silencing cassette of the vector pSIM1678 display two or more desirable traits that are not present in the tubers of untransformed plants of the same variety. In a preferred embodiment, the two or more desirable traits are selected from the group consisting of low asparagine accumulation, reduced black-spot bruising, reduced accumulation of reducing sugars during storage and reduced heat-induced acrylamide formation. In one aspect of the invention, the potato plant variety expressing the two silencing cassettes of the plant DNA vector pSIM1278 and the silencing cassette of the plant DNA vector pSIM1678 is the Russet Burbank W8 variety.

In another aspect of the invention, the potato plant variety W8 of the present invention expresses the late blight resistance gene (Rpi-vnt1) of the plant DNA vector pSIM1678. In a further aspect of the present invention, the potato plant variety W8 of the present invention has increased resistance to late blight infection.

Thus, according to the invention, there is provided a new potato cultivar of the genus and species *Solanum tuberosum* L. designated W8. This invention thus relates to potato cultivar W8, to the tubers of potato cultivar W8, to the plants of potato cultivar W8, to the seeds of potato cultivar W8, to the food products produced from potato cultivar W8, and to methods for producing a potato plant produced by selfing potato cultivar W8 or by crossing potato cultivar W8 with another potato cultivar, and the creation of variants by mutagenesis or transformation of potato cultivar W8.

Thus, any such methods using the cultivar W8 are embodiments of this invention: selfing, backcrosses, hybrid production, crosses to populations, and the like. All plants produced using potato cultivar W8 as at least one parent are within the scope of this invention. Advantageously, the potato cultivar could be used in crosses with other, different, potato plants to produce first generation ($F_1$) potato hybrid tubers, seeds and plants with superior characteristics.

In another embodiment, the present invention provides for single or multiple gene converted plants of potato cultivar W8. In one embodiment, the transferred gene(s) may be a dominant or recessive allele(s). In some embodiments, the transferred gene(s) will confer such traits as herbicide resistance, insect resistance, resistance for bacterial, fungal, or viral disease, male fertility, male sterility, enhanced nutritional quality, uniformity, and increase in concentration of starch and other carbohydrates, decrease in tendency to bruise and decrease in the rate of conversion of starch to sugars. The gene(s) may be a naturally occurring potato gene or a transgene introduced through genetic engineering techniques, backcrossing or mutation.

In another embodiment, the present invention provides regenerable cells for use in tissue culture of potato cultivar W8. In one embodiment, the tissue culture will be capable of regenerating plants having all the physiological and morphological characteristics of the foregoing potato plant, and of regenerating plants having substantially the same genotype as the foregoing potato plant. In some embodiments, the regenerable cells in such tissue cultures will be embryos, protoplasts, meristematic cells, callus, pollen, leaves, anthers, pistils, cotyledons, hypocotyl, roots, root tips, flowers, seeds, petioles, tubers, eyes or stems. Still further, the present invention provides potato plants regenerated from tissue cultures of the invention.

In a further embodiment, the invention provides a food product made from a tuber of potato plant variety Russet Burbank W8. Preferably, the food product is a heat-treated product. Even more preferably, the food product is a French fry, potato chip, dehydrated potato material, potato flakes, or potato granules.

In addition to the exemplary aspects and embodiments described above, further aspects and embodiments will become apparent by study of the following descriptions.

BRIEF DESCRIPTION OF THE DRAWINGS

As seen in FIG. 10, W8 has the trait for black spot bruise reduction, whereas the control does not.

DETAILED DESCRIPTION OF THE INVENTION

Figure 1:
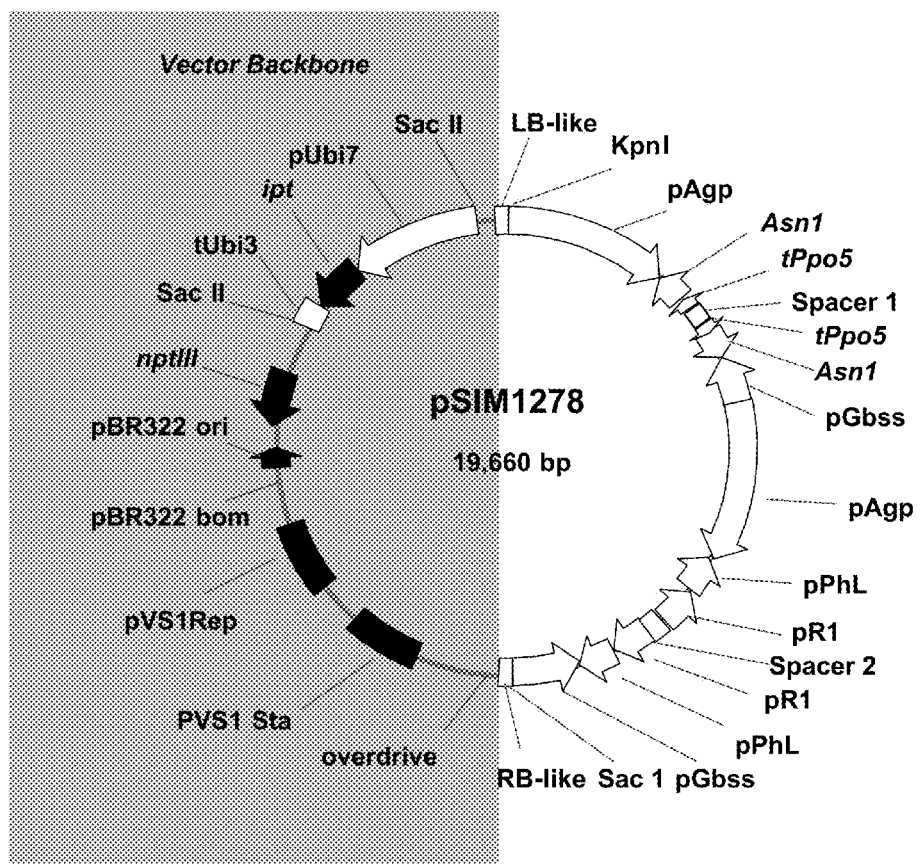
FIG. 1 depicts the pSIM1278 transformation vector. The vector backbone region, on the left, is 9,512 bp long, as it starts at position 10,149 bp and ends at position 19,660 bp. The backbone DNA consists mainly of bacterial DNA which provides support maintenance of the DNA insert prior to plant transformation. The DNA insert region (right side), including flanking Border sequences, is 10,148 bp long (from 1 bp to 10,148 bp). The DNA insert consists of native DNA only and was stably integrated into the potato genome upon transformation.

In the description and tables which follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Amino acid sequence. As used herein, includes an oligopeptide, peptide, polypeptide, or protein and fragments thereof that are isolated from, native to, or naturally occurring in a plant, or are synthetically made but comprise the nucleic acid sequence of the endogenous counterpart.

Artificially manipulated. as used herein, "artificially manipulated" means to move, arrange, operate or control by the hands or by mechanical means or recombinant means, such as by genetic engineering techniques, a plant or plant cell, so as to produce a plant or plant cell that has a different biological, biochemical, morphological, or physiological phenotype and/or genotype in comparison to unmanipulated, naturally-occurring counterpart.

Asexual propagation. Producing progeny by generating an entire plant from leaf cuttings, stem cuttings, root cuttings, tuber eyes, stolons, single plant cells protoplasts, callus and the like, that does not involve fusion of gametes.

Backbone. Nucleic acid sequence of a binary vector that excludes the DNA insert sequence intended for transfer.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bacterial Ring Rot. Bacterial ring rot is a disease caused by the bacterium *Clavibacter michiganense* ssp. Bacterial ring rot derives its name from a characteristic breakdown of the vascular ring within the tuber. This ring often appears as a creamy-yellow to light-brown, cheesy rot. On the outer surface of the potato, severely diseased tubers may show slightly sunken, dry and cracked areas. Symptoms of bacterial ring rot in the vascular tissue of infected tubers can be less obvious than described above, appearing as only a broken, sporadically appearing dark line or as a continuous, yellowish discoloration.

Black spot bruise. Black spots found in bruised tuber tissue are a result of a pigment called melanin that is produced following the injury of cells and gives tissue a brown, gray or black appearance. Melanin is formed when phenol substrates and an appropriate enzyme come in contact with each other as a result of cellular damage. The damage does not require broken cells. However, mixing of the substrate and enzyme must occur, usually when the tissue is impacted. Black spots occur primarily in the perimedullary tissue just beneath the vascular ring, but may be large enough to include a portion of the cortical tissue.

Border-like sequences. A "border-like" sequence is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A DNA insert of the present invention preferably contains border-like sequences. A border-like sequence of a DNA insert is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. A DNA insert left and right border sequence are isolated from and/or native to the genome of a plant that is to be modified. A DNA insert border-like sequence is not identical in nucleotide sequence to any known *Agrobacterium*-derived T-DNA border sequence. Thus, a DNA insert border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a DNA insert border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "DNA insert border" and "DNA insert border-like" are exchangeable. A border-like sequence can be isolated from a plant genome and be modified or mutated to change the efficiency by which it is capable of integrating a nucleotide sequence into another nucleotide sequence. Other polynucleotide sequences may be added to or incorporated within a border-like sequence of the present invention. Thus, a DNA insert left border or a DNA insert right border may be modified so as to possess 5'- and 3'-multiple cloning sites, or additional restriction sites. A DNA insert border sequence may be modified to increase the likelihood that backbone DNA from the accompanying vector is not integrated into the plant genome.

Consisting essentially of. A composition "consisting essentially of" certain elements is limited to the inclusion of those elements, as well as to those elements that do not materially affect the basic and novel characteristics of the inventive composition. Thus, so long as the composition does not affect the basic and novel characteristics of the instant invention, that is, does not contain foreign DNA that is not from the selected plant species or a plant that is sexually compatible with the selected plant species, then that composition may be considered a component of an inventive composition that is characterized by "consisting essentially of" language.

Cotyledon. A cotyledon is a type of seed leaf. The cotyledon contains the food storage tissues of the seed.

Degenerate primer. A "degenerate primer" is an oligonucleotide that contains sufficient nucleotide variations that it can accommodate base mismatches when hybridized to sequences of similar, but not exact, homology.

Dicotyledon (dicot). A flowering plant whose embryos have two seed leaves or cotyledons. Examples of dicots include, but are not limited to, tobacco, tomato, potato, sweet potato, cassava, legumes including alfalfa and soybean, carrot, strawberry, lettuce, oak, maple, walnut, rose, mint, squash, daisy, and cactus.

DNA insert. According to the present invention, the DNA insert to be inserted into the genome of a plant comprises polynucleotide sequences native to that plant or has native genetic elements to that plant. In one example, for instance, the DNA insert from pSIM1278 of the potato variety W8 of the present invention is a 10,148 bp non-coding polynucleotide that is native to potato or wild potato, a potato sexually-compatible plant, that is stably integrated into the genome of the plant cells upon transformation and silences genes involved in the expression of black spot bruises, asparagine accumulation and senescence sweetening. The DNA insert preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. A second DNA insert comes from the transformation vector referred to as pSIM1678 that comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. These expression cassettes contain no foreign DNA, and consist of DNA only from either the selected plant species or from a plant that is sexually compatible with the selected plant species.

Embryo. The embryo is the immature plant contained within a mature seed.

Foreign. "Foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a desired intragenic plant is one that does not contain any foreign nucleic acids integrated into its genome.

Gene. As used herein, "gene" refers to the coding region and does not include nucleotide sequences that are 5'- or 3'- to that region. A functional gene is the coding region operably linked to a promoter or terminator. A gene can be introduced into a genome of a species, whether from a different species or from the same species, using transformation or various breeding methods.

Gene Converted (Conversion). Gene converted (conversion) plant refers to plants which are developed by a plant breeding technique called backcrossing wherein essentially all of the desired morphological and physiological characteristics of a variety are recovered in addition to the one or more genes transferred into the variety via the backcrossing technique, via genetic engineering or via mutation. One or more loci may also be transferred.

Genetic rearrangement. Refers to the re-association of genetic elements that can occur spontaneously in vivo as well as in vitro which introduce a new organization of genetic material. For instance, the splicing together of polynucleotides at different chromosomal loci, can occur spontaneously in vivo during both plant development and sexual recombination. Accordingly, recombination of genetic elements by non-natural genetic modification techniques in vitro is akin to recombination events that also can occur through sexual recombination in vivo.

Golden nematode. *Globodera rostochiensis*, commonly known as golden nematode, is a plant parasitic nematode affecting the roots and tubers of potato plants. Symptoms include poor plant growth, wilting, water stress and nutrient deficiencies.

Hypocotyl. A hypocotyl is the portion of an embryo or seedling between the cotyledons and the root. Therefore, it can be considered a transition zone between shoot and root.

In frame. Nucleotide triplets (codons) are translated into a nascent amino acid sequence of the desired recombinant protein in a plant cell. Specifically, the present invention contemplates a first nucleic acid linked in reading frame to a second nucleic acid, wherein the first nucleotide sequence is a gene and the second nucleotide is a promoter or similar regulatory element.

Integrate. Refers to the insertion of a nucleic acid sequence from a selected plant species, or from a plant that is from the same species as the selected plant, or from a plant that is sexually compatible with the selected plant species, into the genome of a cell of a selected plant species. "Integration" refers to the incorporation of only native genetic elements into a plant cell genome. In order to integrate a native genetic element, such as by homologous recombination, the present invention may "use" non-native DNA as a step in such a process. Thus, the present invention distinguishes between the "use of" a particular DNA molecule and the "integration" of a particular DNA molecule into a plant cell genome.

Introduction. As used herein, refers to the insertion of a nucleic acid sequence into a cell, by methods including infection, transfection, transformation or transduction.

Isolated. "Isolated" refers to any nucleic acid or compound that is physically separated from its normal, native environment. The isolated material may be maintained in a suitable solution containing, for instance, a solvent, a buffer, an ion, or other component, and may be in purified, or unpurified, form.

Late blight. A potato disease caused by the oomycete *Phytophthora infestans* and also known as 'potato blight' that can infect and destroy the leaves, stems, fruits, and tubers of potato plants.

Leader. Transcribed but not translated sequence preceding (or 5' to) a gene.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marketable Yield. Marketable yield is the weight of all tubers harvested that are between 2 and 4 inches in diameter. Marketable yield is measured in cwt (hundred weight) where cwt=100 pounds.

Monocotyledon (monocot). A flowering plant whose embryos have one cotyledon or seed leaf. Examples of monocots include, but are not limited to turf grass, maize, rice, oat, wheat, barley, sorghum, orchid, iris, lily, onion, and palm.

Native. A "native" genetic element refers to a nucleic acid that naturally exists in, orginates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence. A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Native genetic elements. "Native genetic elements" can be incorporated and integrated into a selected plant species genome according to the present invention. Native genetic elements are isolated from plants that belong to the selected plant species or from plants that are sexually compatible with the selected plant species. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*).

Naturally occurring nucleic acid. Naturally occurring nucleic acid are found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked. Combining two or more molecules in such a fashion that in combination they function properly in a plant cell. For instance, a promoter is operably linked to a structural gene when the promoter controls transcription of the structural gene.

Plant. As used herein, the term "plant" includes but is not limited to angiosperms and gymnosperms such as potato, tomato, tobacco, alfalfa, lettuce, carrot, strawberry, sugarbeet, cassava, sweet potato, soybean, maize, turf grass, wheat, rice, barley, sorghum, oat, oak, eucalyptus, walnut, and palm. Thus, a plant may be a monocot or a dicot. The word "plant," as used herein, also encompasses plant cells, seed, plant progeny, propagule whether generated sexually or asexually, and descendents of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

Plant Parts. As used herein, the term "plant parts" (or a potato plant, or a part thereof) includes but is not limited to protoplast, leaf, stem, root, root tip, anther, pistil, seed, embryo, pollen, ovule, cotyledon, hypocotyl, flower, tuber, eye, tissue, petiole, cell, meristematic cell, and the like.

Plant species. The group of plants belonging to various officially named plant species that display at least some sexual compatibility.

Plant transformation and cell culture. Broadly refers to the process by which plant cells are genetically modified and transferred to an appropriate plant culture medium for maintenance, further growth, and/or further development.

Precise breeding. Refers to the improvement of plants by stable introduction of nucleic acids, such as native genes and regulatory elements isolated from the selected plant species, or from another plant in the same species as the selected plant, or from species that are sexually compatible with the selected plant species, into individual plant cells, and subsequent regeneration of these genetically modified plant cells into whole plants. Since no unknown or foreign nucleic acid is permanently incorporated into the plant genome, the inventive technology makes use of the same genetic material that is also accessible through conventional plant breeding.

Progeny. As used herein, includes an $F_1$ potato plant produced from the cross of two potato plants where at least one plant includes potato cultivar W8 and progeny further includes, but is not limited to, subsequent $F_2$, $F_3$, $F_4$, $F_5$, $F_6$, $F_7$, $F_8$, $F_9$, and W8 generational crosses with the recurrent parental line.

Quantitative Trait Loci (QTL). Quantitative trait loci (QTL) refer to genetic loci that control to some degree numerically representable traits that are usually continuously distributed.

Recombinant. As used herein, broadly describes various technologies whereby genes can be cloned, DNA can be sequenced, and protein products can be produced. As used herein, the term also describes proteins that have been produced following the transfer of genes into the cells of plant host systems.

Regeneration. Regeneration refers to the development of a plant from tissue culture.

Regulatory sequences. Refers to those sequences which are standard and known to those in the art that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 *J. Biol. Chem.* 3731-38, 1985; Cornejo et al., 23 *Plant Mol. Biol.* 567: 81, 1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified.

Selectable marker. A "selectable marker" is typically a gene that codes for a protein that confers some kind of resistance to an antibiotic, herbicide or toxic compound, and is used to identify transformation events. Examples of selectable markers include the streptomycin phosphotransferase (spt) gene encoding streptomycin resistance, the phosphomannose isomerase (pmi) gene that converts mannose-6-phosphate into fructose-6 phosphate; the neomycin phosphotransferase (nptII) gene encoding kanamycin and geneticin resistance, the hygromycin phosphotransferase (hpt or aphiv) gene encoding resistance to hygromycin, acetolactate synthase (als) genes encoding resistance to sulfonylurea-type herbicides, genes coding for resistance to herbicides which act to inhibit the action of glutamine synthase such as phosphinothricin or basta (e.g., the bar gene), or other similar genes known in the art.

Sense suppression. Reduction in expression of an endogenous gene by expression of one or more an additional copies of all or part of that gene in transgenic plants.

Specific gravity. As used herein, "specific gravity" is an expression of density and is a measurement of potato quality. There is a high correlation between the specific gravity of the tuber and the starch content and percentage of dry matter or total solids. A higher specific gravity contributes to higher recovery rate and better quality of the processed product.

T-DNA-Like. A "T-DNA-like" sequence is a nucleic acid that is isolated from a selected plant species, or from a plant that is sexually compatible with the selected plant species, and which shares at least 75%, 80%, 85%, 90%, or 95%, but not 100%, sequence identity with *Agrobacterium* species T-DNA. The T-DNA-like sequence may contain one or more border or border-like sequences that are each capable of integrating a nucleotide sequence into another polynucleotide.

Total Yield. Total yield refers to the total weight of all harvested tubers.

Trailer. Transcribed but not translated sequence following (or 3' to) a gene.

Transcribed DNA. DNA comprising both a gene and the untranslated leader and trailer sequence that are associated with that gene, which is transcribed as a single mRNA by the action of the preceding promoter.

Transformation of plant cells. A process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

Transgene. A gene that will be inserted into a host genome, comprising a protein coding region. In the context of the instant invention, the elements comprising the transgene are isolated from the host genome.

Transgenic plant. A genetically modified plant which contains at least one transgene.

Variant. A "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

Vine Maturity. Vine maturity refers to a plant's ability to continue to utilize carbohydrates and photosynthesize. Vine maturity is scored on a scale of 1 to 5 where 1=dead vines and 5=vines green, still flowering.

The insertion of desirable traits into the genome of potato plants presents particular difficulties because potato is tetraploid, highly heterozygous and sensitive to in-breeding depression. It is therefore very difficult to efficiently develop transgenic potato plants that produce less acrylamide and less harmful Maillard-reaction products, including N-Nitroso-N-

(3-keto-1,2-butanediol)-3'-nitrotyramine (Wang et al., *Arch Toxicol* 70: 10-5, 1995), 5-hydroxymethyl-2-furfural (Janzowski et al., *Food Chem Toxicol* 38: 801-9, 2000), and other Maillard reaction products with mutagenic properties (Shibamoto, *Prog Clin Biol Res* 304: 359-76, 1989), during processing using conventional breeding.

Several methods have been tested and research is ongoing to reduce acrylamide through process changes, reduction in dextrose, and additives such as asparaginase, citrate, and competing amino acids. The required capital expense to implement process changes throughout the potato industry would cost millions of dollars. In addition to the expense, these process changes have significant drawbacks including potentially negative flavors associated with additives such as asparaginase or citrate. Typically, fry manufacturers add dextrose during processing of french fries to develop the desired golden brown color, but dextrose also increases the formation of acrylamide through the Maillard reaction. Significant reductions in acrylamide occur by merely omitting dextrose from the process; however, the signature golden brown colors must then be developed some other way (such as though the addition of colors like annatto) The use of alternate colors, results in an absence of the typical flavors that develop through those browning reactions. Another challenge with the use of additives to reduce reactants like asparagine is moisture migration that occurs during frozen storage with the resulting return of asparagine to the surface and increased acrylamide. Finally, the blackening that occurs after potatoes are bruised affects quality and recovery in processing French fries and chips. Damaged and bruised potatoes must be trimmed or are rejected before processing, resulting in quality challenges or economic loss.

The "native technology" strategy of the present invention addresses the need of the potato industry to improve the agronomic characteristics and nutritional value of potatoes by reducing the expression of polyphenol oxidase-5 (PPO-5), which is responsible for black spot bruise, the expression of asparagine synthetase-1 (Asn-1), which is responsible for the accumulation of asparagine, a precursor in acrylamide formation, reducing the expression of the enzyme vacuolar invertase, which converts sucrose into glucose and fructose, and/or the expression of phosphorylase-L and kinase-R1, which are enzymes associated with the accumulation of reducing sugars that normally react with amino acids, such as asparagine, and form toxic Maillard products, including acrylamide. The partial or complete silencing of these genes in tubers decreases the potential to produce acrylamide. Use of the native technology of the invention allows for the incorporation of desirable traits into the genome of commercially valuable potato plant varieties by transforming the potatoes only with "native" genetic material, that is genetic material obtained from potato plants or plants that are sexually-compatible with potato plants, that contains only non-coding regulatory regions, without the integration of any foreign genetic material into the plant's genome. Desirable traits include high tolerance to impact-induced black spot bruise, increased resistance to late blight infection, reduced formation of the acrylamide precursor asparagine and reduced accumulation of reducing sugars, with consequent decrease in accumulation of toxic Maillard products, including acrylamide, improved quality and food color control. The incorporation of these desirable traits into existing potato varieties is impossible to achieve through traditional breeding because potato is tetraploid, highly heterozygous and sensitive to inbreeding depression.

The non-coding potato plant DNA insert sequences used in the present invention are native to the potato plant genome and do not contain any *Agrobacterium* DNA. One of the DNA inserts preferably comprises two expression cassettes and is inserted into a transformation vector referred to as the pSIM1278 transformation vector. The first cassette comprises fragments of both the asparagine synthetase-1 gene (Asn1) and the polyphenol oxidase-5 gene (Ppo5), arranged as inverted repeats between the Agp promoter of the ADP glucose pyrophosphorylase gene (Agp) and the Gbss promoter of the granule-bound synthase gene (Gbss). These promoters are predominantly active in tubers. The function of the second cassette is to silence the promoters of the starch associated gene dikinase-R1 (R1) and the phosphorylase-L gene (PhL). This cassette is comprised of fragments of the promoters of the starch associated gene dikinase-R1 (R1) and the phosphorylase-L gene (PhL), operably linked to the same Agp and Gbss promoters as the first cassette. These expression cassettes contain no foreign DNA, and consist of DNA only from either the selected plant species or from a plant that is sexually compatible with the selected plant species. A second DNA insert comes from the transformation vector referred to as pSIM1678 that comprises the Rpi-vnt1 expression cassette and a silencing cassette for the plant vacuolar invertase gene, VInv. The Rpi-vnt1 gene cassette consists of the VNT1 protein coding region regulated by its native promoter and terminator sequences to confer broad resistance to late blight, whereas the silencing cassette consists of an inverted repeat of sequence from the potato VInv gene flanked by opposing plant promoters, pGbss and pAgp. The function of the first cassette is to confer resistance to late blight, while the function of the second cassette is to silence the vacuolar invertase gene, reducing glucose and fructose.

The commercially valuable potato plant variety used in the present invention is Russet Burbank. Luther Burbank developed this variety in the early 1870s. Plants are vigorous and continue vine growth throughout the season. Stems are thick, prominently angled and finely mottled. Leaflets are long to medium in width and light to medium green in color. The blossoms are few, white and not fertile. The cultivar is tolerant to common scab but is susceptible to *Fusarium* and *Verticillium* wilts, leafroll and net necrosis, potato virus Y and late blight. Plants require conditions of high and uniform soil moisture and controlled nitrogen fertility to produce tubers free from knobs, pointed ends and dumbbells. Jelly-end and sugar-end develop in tubers when plants are subjected to stress. The tubers produced are large brown-skinned and white-fleshed, display good long-term storage characteristics, and represent the standard for excellent baking and processing quality. Russett Burbank varieties have a high susceptibility to develop black spot bruise and also have high free asparagine content and high senescence sweetening potential (Am. J. Potato Res (1966) 43: 305-314). The variety is sterile and widely grown in the Northwest and Midwest, especially for the production of French fries.

The present invention provides a potato variety of significant market value—namely Russet Burbank—transformed with the transformation vector pSIM1278 followed by transformation with a second transformation vector pSIM1678, identified using the polymerase chain reaction rather than markers, and successfully propagated. Also provided are food products made from the tubers of the potato plant variety W8 of the present invention. Potato cultivar W8 has the following unique plant variety identifier with the Organization for Economic Cooperation and Development (OECD): SPS-ØØØW8-4.

Targeted gene silencing with native DNA reduces the level of the RNA transcripts of the targeted genes in the tubers of the potato plant variety W8. Potato cultivar W8 contains expression cassettes that lower levels of reducing sugars in tubers by multiple mechanisms. Through the transformation with pSIM1278, silencing cassettes were introduced for the promoters of the starch associated gene (R1) and the phosphorylase-L gene (PhL), while transformation with pSIM1678 introduced a silencing cassette for the invertase gene (VInv; Ye et al., 2010). Together, these traits function by slowing the conversion of starch and sucrose to reducing sugars (glucose and fructose).

Thus, the tubers of the potato plant variety W8 of the invention incorporate highly desirable traits, including a reduced ratio in free amide amino acids asparagine and glutamine, which is associated with reduced acrylamide formation upon frying or baking Specifically, the potato variety W8 of the present invention is characterized by two- to more than four-fold reduction in free-asparagine content, reduced discoloration associated with black spot bruise and increased resistance to late blight. Furthermore, the potato variety W8 of the invention displays a delay in the degradation of starch into the reducing sugars glucose and fructose during storage. Impairment of starch-to-sugar conversion further reduces senescence sweetening and acrylamide formation and limits heat-induced browning.

Potato variety W8 of the present invention is therefore extremely valuable in the potato industry and food market, as its tubers produce significantly less acrylamide upon heat processing and do not carry any potentially harmful foreign genes.

EXAMPLES

The present invention uses native technology to integrate native non-coding DNA into the genome of selected potato plant varieties to develop new intragenic potato plant varieties. The method includes trait identification, design of vectors, incorporation of vectors into *Agrobacterium*, selection of the recipient potato variety, plant transformation, evidence of absence of open reading frames, and confirmation that the new potato plant varieties contain only the native DNA. The potato cultivar W8 of the present invention has a lowered potential to form acrylamide, lower amounts of sucrose and is more resistant to black spot bruise than its untransformed counterpart. Additionally, potato cultivar W8 of the present invention has increased resistance to late blight.

Example 1

The pSIM1278 Transformation Vector

The transformation vector pSIM1278 used in the invention was derived from pSIM106, which was created by ligating a 0.4-kb potato plant DNA fragment (deposited as GenBank accession no. AY566555) with a 5.9-kb SacII-SphI fragment of pCAMBIA1301 (CAMBIA, Canberra, Australia), carrying bacterial origins of replication from plasmids pVS1 and pBR322, and the nptIII gene for bacterial resistance to kanamycin. An expression cassette comprising the *Agrobacterium* ipt gene preceded by the Ubi-3 promoter (Garbarino and Belknap, 1994) and followed by the Ubi-3 terminator was introduced as a 2.6-kb SacII fragment into the vector backbone (Rommens et al., 2004). Insertion of the native 10-kb DNA segment carrying two silencing cassettes into the DNA insert of pSIM106 yielded pSIM1278. This vector was used for all transformations. The pSIM1278 vector map is shown in FIG. 1. The vector backbone region is 9,512 bp, as it starts at position 10,149 bp and ends at position 19,660 bp. The backbone DNA consists mainly of bacterial DNA and provides support maintenance of the DNA insert prior to plant transformation. The backbone portion is not transferred into the plant cells. The various elements of the backbone are described in Table 1. The general structure map of pCAMBIA vectors can be found at http://www.cambia.org/daisy/cambia/585.html.

TABLE 1

| Genetic Element | Origin | Accession Number | Position (pSIM1278) | Function |
| --- | --- | --- | --- | --- |
| SacII restriction site | *S. tuberosum* | AJ272136.1 | 19,411-19,416 | Restriction site used to connect Ubi7 promoter with LB flanking sequence. |
| Polyubiquitin promoter (Ubi7) including the coding sequence for a 76- amino-acid potato ubiquitin monomer (UBQmon) | *S. tuberosum* var. Ranger Russet | U26831.1 | 17,671-19,410 | Promoter to drive expression of the ipt backbone marker gene |
| Isopentenyl transferase (ipt) gene | *Agrobacterium tumefaciens* | NC_002377.1 | 16,936-17,658 | Condensation of AMP and isopentenylpyrophosphate to form isopentenyl-AMP, a cytokinin in the plant. Results in abnormal growth phenotypes in plant (Smigocki and Owens 1988) |
| Terminator of the ubiquitin-3 gene (tUbi3) | *S. tuberosum* | GP755544.1 | 16,230-16,584 | Terminator for ipt gene transcription (Garbarino and Belknap 1994) |
| Neomycin phosphotransferase III (nptIII) gene | *E. coli* | FJ362602.1 | 15,240-16,034 | Aminoglycoside phosphotransferase (Courvalin et al. 1977) |
| Origin of replication for pBR322 (pBR322 ori) | *E. coli* | J01784.1 | 14,669-14,949 | Bacterial origin of replication |
| (pBR322 bom) | *E. coli* | J01749.1 | 14,269-14,529 | pBR322 region for replication in *E. coli* |
| pVS1 replicon (pVS1Rep) | *Pseudomonas fluorescens* plasmid pVS1 | AJ537514.1 (4,501-5,501) | 12,859-13,859 | pVS1 region for replication in *Agrobacterium* |
| pVS1 partitioning protein StaA (PVS1 Sta) | *Pseudomonas fluorescens* plasmid pVS1 | AJ537514.1 (6,095-7,095) | 11,266-12,266 | pVS1 stability |

TABLE 1-continued

| Genetic Element | Origin | Accession Number | Position (pSIM1278) | Function |
|---|---|---|---|---|
| Overdrive | *Agrobacterium tumefaciens* | K00549.1 (103-132) | 10,155-10,184 | Enhances cleavage at the Right Border site |

Example 2

The pSIM1278 Plant DNA Insert and its Open Reading Frames (ORFs)

Figure 2:
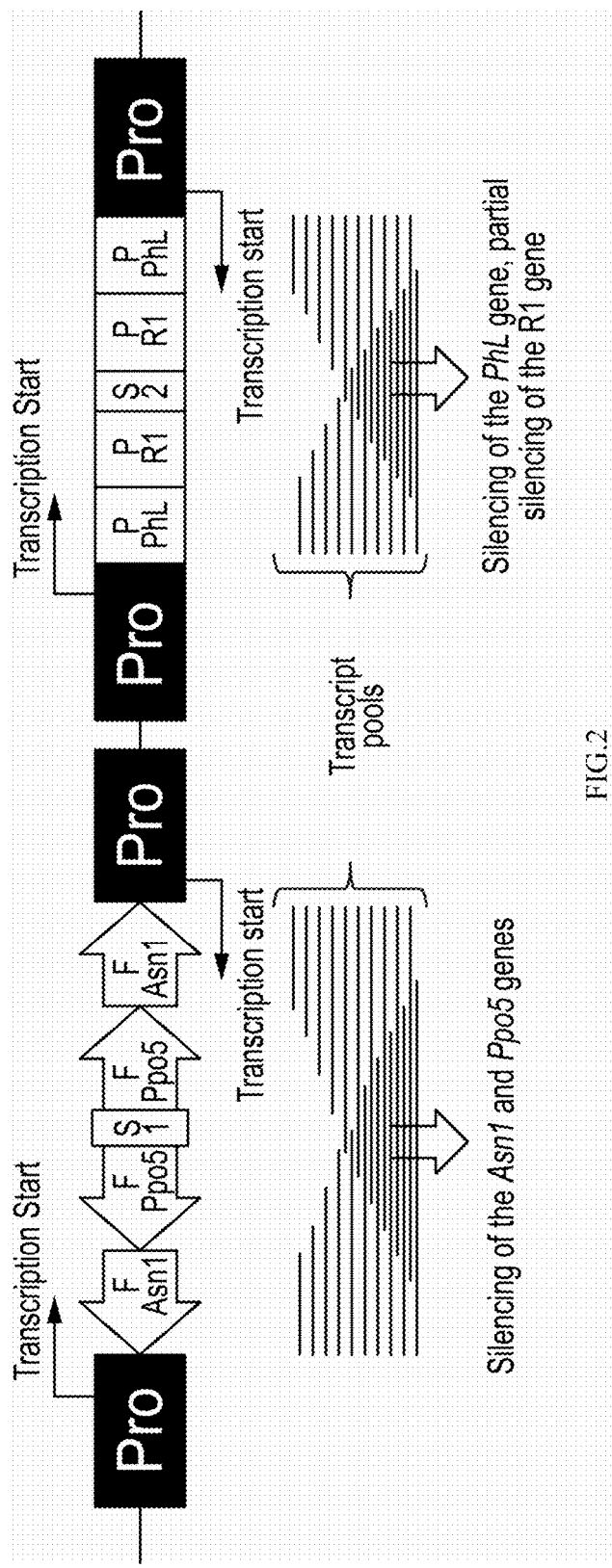
FIG. 2 provides a schematic representation of the silencing cassettes in the DNA insert inserted in the pSIM1278 transformation vector. Each silencing cassette contains two copies of two gene fragments separated by a spacer. Two copies of a DNA segment comprising fragments of four targeted genes, namely Asn-1, Ppo-5, Ph1 and R1, were inserted as inverted repeats between two convergent promoters, indicated as Pro, that are predominantly active in tubers. Plants containing the resulting silencing cassette produce a diverse and unpolyadenylated array of RNA molecules in tubers that dynamically and vigorously silence the intended target genes. The size of the RNA molecules was generally smaller than the distance between the two promoters employed because convergent transcription results in collisional transcription.

The pSIM1278 DNA insert region, including the flanking border sequences, used in the pSIM1278 is 10,148 bp long, from 1 bp to 10,148 bp. The pSIM1278 DNA insert consists of native DNA only and is stably integrated into the potato genome. The pSIM1278 DNA insert or a functional part thereof, is the only genetic material of vector pSIM1278 that is integrated in the potato plant varieties of the invention. The pSIM1278 DNA insert is described in FIG. 2 and Table 2 below. The LB and RB sequences (25 bp each) were synthetically designed to be similar to and function like T-DNA borders from *Agrobacterium tumefaciens*. The GenBank Accession AY566555 was revised to clarify the sources of DNA for the Border regions. ASN1 described as genetic elements 5 and 10 is referred to as StAst1 in Chawla et al., 2012.

TABLE 2

| Genetic Element | Origin | Accession Number | Position (pSIM1278) | Intended Function |
|---|---|---|---|---|
| 1. Left Border (LB) site1 | Synthetic | AY566555 (bases 1-25) | 1-25 | Site for secondary cleavage to release single-stranded DNA insert from pSIM1278 (van Haaren et al. 1989) |
| 2. Left Border region sequence including LB | *S. tuberosum* var. Ranger Russet. | AY566555 (basesl-187) | 1-187 | Supports secondary cleavage at LB |
| 3. KpnI restriction site | *S. tuberosum* | AF393847.1 | 188-193 | Site for connection of DNA insert with LB flanking sequence. |
| 4. Promoter for the ADP glucose pyrophosphorylase gene (pAgp), 1st copy | *S. tuberosum* var. Ranger Russet | HM363752 | 194-2,453 | One of the two convergent promoters that drives expression of an inverted repeat containing fragments of Asn1 and Ppo5, especially in tubers |
| 5. Fragment of the asparagine synthetase-1 (Asn1) gene (1st copy antisense orientation) | *S. tuberosum* var. Ranger Russet | HM363759 | 2,454-2,858 | Generates with (10) double stranded RNA that triggers the degradation of Asn1 transcripts to impair asparagine formation (Chawla et al. 20123) |
| 6. 3'-untranslated sequence of the polyphenol oxidase-5 gene (Ppo5) (1st copy, in antisense orientation) | *S. verrucosum* | HM363754 | 2,859-3,002 | Generates with (9) double stranded RNA that triggers the degradation of Ppo5 transcripts to block black spot development |
| 7. XbaI restriction site | *S. tuberosum* | DQ478950.1 | 3,003-3,008 | Site for connection of the first Ppo5 copy to spacer-1. |
| 8. Spacer-1 | *S. tuberosum* var. Ranger Russet | HM363753 | 3,009-3,166 | Sequence between the 1st inverted repeats |
| 9. 3'-untranslated sequence of the polyphenol oxidase-5 gene (Ppo5) (2nd copy, in sense orientation) | *S. verrucosum* | HM363754 | 3,167-3,310 | Generates with (6) double stranded RNA that triggers the degradation of Ppo5 transcripts to block black spot development |
| 10. Fragment of the asparagine synthetase-1 (Asn1) gene (2nd copy, in sense orientation) | *S. tuberosum* var. Ranger Russet | HM363759 | 3,311-3,715 | Generates with (5) double stranded RNA that triggers the degradation of Asn1 transcripts to impair asparagine formation (Chawla et al. 20123) |
| 11. EcoRI restriction site | *S. tuberosum* var. Ranger Russet | X73477 | 3,716-3,721 | Site for connection of the second Asn1 copy to Gbss promoter. |
| 12. Promoter for the granule-bound starch synthase (pGbss) gene (1st copy, convergent orientation relative to the 1st copy of pAgp) | *S. tuberosum* var. Ranger Russet | HM363755 | 3,722-4,407 | One of the two convergent promoters that drives expression of an inverted repeat containing fragments of Asn1 and Ppo5, especially in tubers |
| 13. Spe1/KpnI restriction sites | *S. tuberosum* var. Ranger Russet | X95996/ AF393847.1 | 4,408-4,423 | Polylinker site for connection of Gbss promoter to the second Agp promoter. |

TABLE 2-continued

| Genetic Element | Origin | Accession Number | Position (pSIM1278) | Intended Function |
|---|---|---|---|---|
| 14. pAgp, 2nd copy | S. tuberosum var. Ranger Russet | HM363752 | 4,424-6,683 | One of the two convergent promoters that drives expression of an inverted repeat containing fragments of the promoters of PhL and R1, especially in tubers |
| 15. Fragment of promoter for the potato phosphorylase-L (pPhL) gene (1st copy, in antisense orientation) | S. tuberosum var. Ranger Russet | HM363758 | 6,684-7,192 | Generates with (20) double stranded RNA that triggers the degradation of PhL transcripts to limit the formation of reducing sugars through starch degradation |
| 16. Fragment of promoter for the potato R1 gene (pR1) (1st copy, in antisense orientation) | S. tuberosum var. Ranger Russet | HM363757 | 7,193-7,724 | Generates with (19) double stranded RNA that triggers the degradation of R1 transcripts to limit the formation of reducing sugars through starch degradation |
| 17. Pst1 restriction site | S. tuberosum var. Ranger Russet | DQ478950.1 | 7,725-7,730 | Site for connection of the first R1 promoter fragment to the spacer2 |
| 18. Spacer-2 | S. tuberosum var. Ranger Russet | HM363756 | 7,731-7,988 | Sequence between the 2nd inverted repeat |
| 19. Fragment of promoter for the potato R1 gene (pR1) (2nd copy, in sense orientation) | S. tuberosum var. Ranger Russet | HM363757 | 7,989-8,520 | Generates with (16) double stranded RNA that triggers the degradation of R1 transcripts to limit the formation of reducing sugars through starch degradation |
| 20. Fragment of promoter for the potato phosphorylase-L (pPhL) gene (2nd copy, in sense orientation) | S. tuberosum var. Ranger Russet | HM363758 | 8,521-9,029 | Generates with (15) double stranded RNA that triggers the degradation of PhL transcript to limit the formation of reducing sugars through starch degradation |
| 21. pGbss (2nd copy, convergent orientation relative to the 2nd copy of pAgp) | S. tuberosum var. Ranger Russet | HM363755 | 9,030-9,953 | One of the two convergent promoters that drives expression of an inverted repeat containing fragments of the promoters of PhL and R1, especially in tubers |
| 22. SacI restriction site | S. tuberosum | AF143202 | 9,954-9,962 | Site for connection of DNA insert with RB flanking sequence. |
| 23. Right Border region sequence including RB | S. tuberosum var. Ranger Russet | AY566555 (bases 231-416) | 9,963-10,148 | Supports primary cleavage at RB-Like site |
| 24. Right Border (RB) sequence1 | Synthetic | AY566555 (bases 392-416) | 10,124-10,148 | Site for primary cleavage to release single stranded DNA insert from pSIM1278 (van Haaren et al. 1989) |

The DNA insert described in Table 2 that was used to create potato line W8 of the present invention does not activate adjacent genes and does not adversely affect the phenotype of potato plant variety W8. In addition, the potato plant variety W8 of the invention does not produce novel proteins associated with open reading frames encoded by the DNA insert.

Example 3

The pSIM1678 Transformation Vector

Figure 3:
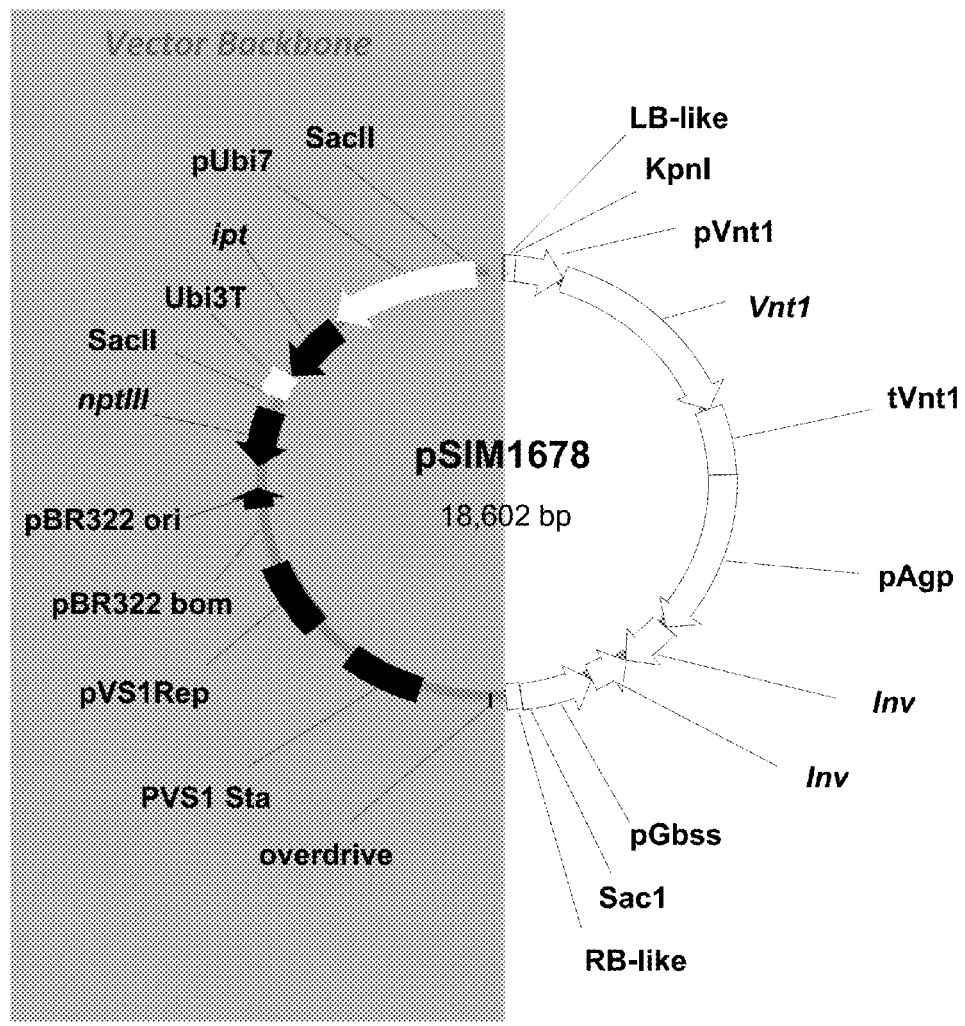
FIG. 3 depicts the pSIM1678 transformation vector of the present invention. The vector backbone region, on the left, is 9,512 bp long, as it starts at position 9,091 bp and ends at position 18,602 bp. The backbone DNA consists mainly of bacterial DNA which provides support maintenance of the DNA insert prior to plant transformation. The DNA insert region (right side), including flanking Border sequences, is 9,090 bp long (from 1 bp to 9,090 bp). The DNA insert consists of native DNA only and was stably integrated into the potato genome upon transformation.

The transformation vector pSIM1678 used in the invention was transformed using the same methods described for pSIM1278 in Example 1. The pSIM1678 vector map is shown in FIG. 3. The vector backbone region is 9,512 bp, as it starts at position 9,091 bp and ends at position 18,602 bp. The backbone DNA consists mainly of bacterial DNA and provides support maintenance of the DNA insert prior to plant transformation. The backbone portion is not transferred into the plant cells. The various elements of the backbone are described in Table 1. Although the numbering system shown in Table 1 is based on pSIM1278, the backbone sequences are identical for pSIM1678.

Example 4

The pSIM1678 Plant DNA Insert and its Open Reading Frames (ORFs)

The pSIM1678 DNA insert region, including the flanking border sequences, used in the pSIM1678 is 9,090 bp long (from 1 bp to 9,090 bp). The pSIM1678 DNA insert consists of native DNA only and is stably integrated into the potato genome. The pSIM1678 DNA insert or a functional part thereof, is the only genetic material of vector pSIM1678 that is integrated in the potato plant varieties of the invention. The pSIM1678 DNA insert is described in FIG. 3 and Table 3 below. In Table 3, the LB and RB sequences (25-bp each) were synthetically designed to be similar to and function like T-DNA borders from *Agrobacterium tumefaciens*. GenBank Accession AY566555 was revised to clarify the sources of DNA for the Border regions.

TABLE 3

| Genetic Element | Origin | Accession Number | Position (pSIM1678) | Intended Function |
|---|---|---|---|---|
| 1. Left Border (LB) site | Synthetic | AY566555 (bases 1-25) | 1-25 | Site for secondary cleavage to release single-stranded DNA insert from pSIM1678 |
| 2. Left Border region sequence including LB | S. tuberosum var. Ranger Russet | AY566555 (bases 1-187) | 1-187 | Supports secondary cleavage at LB |
| 3. KpnI restriction site | S. tuberosum | AF393847.1 | 188-193 | Site for connection of DNA insert with LB flanking sequence. |
| 4. Native promoter for the late blight resistance gene (Rpi-vnt1) | S. venturii | FJ423044.1 | 194-902 | Drives expression of late blight resistance gene vnt1 |
| 5. Late blight resistance gene (Rpi-vnt1) | S. venturii | FJ423044.1 | 903-3,578 | *Solanum venturii* late blight resistance protein gene |
| 6. Native terminator for the Rpi-vnt1 gene | S. venturii | FJ423044.1 | 3,579-4,503 | Ends transcription of late blight resistance gene vnt1 |
| 7. ApaI | S. tuberosum | HM363755 | 4,504-4,509 | Site for connection of vnt1 terminator with Agp promoter |
| 8. Promoter for the ADP glucose pyrophosphorylase gene (pAgp) | S. tuberosum var. Ranger Russet | HM363752 | 4,510-6,770 | One of the two convergent promoters that drives expression of an inverted repeat containing fragments of acid invertase gene. |
| 9. BamH1 | S. tuberosum var. Ranger Russet | DQ206630 | 6,771-6,776 | Site for connection of Agp promoter with invertase |
| 10. Fragment of the acid invertase (sense orientation) | S. tuberosum var. Ranger Russet | DQ478950.1 | 6,777-7,455 | Generates with (12) double stranded RNA that triggers the degradation of invertase transcripts |
| 11. EcoRI | S. tuberosum var. Ranger Russet | X73477 | 7,456-7,461 | Site for connection of an invertase fragment (sense) with an invertase fragment (anti-sense) |
| 12. Fragment of the acid invertase (anti-sense orientation) | S. tuberosum var. Ranger Russet | DQ478950.1 | 7,462-7,965 | Generates with (10) double stranded RNA that triggers the degradation of invertase transcripts |
| 13. Spe1 | S. tuberosum var. Ranger Russet | X95996 | 7,966-7,971 | Site for connection of an invertase fragment (anti-sense) with GBSS promoter |
| 14. Promoter for the granule-bound starch synthase (pGbss) gene (convergent orientation relative to the pAgp) | S. tuberosum var. Ranger Russet | HM363755 | 7,972-8,895 | One of the two convergent promoters that drives expression of an inverted repeat containing fragments of invertase gene, especially in tubers |
| 15. SacI restriction site | S. tuberosum | AF143202 | 8,896-8,901 | Site for connection of DNA insert with RB flanking sequence. |
| 16. Right Border region sequence including RB | S. tuberosum var. Ranger Russet | AY566555 (bases 231-416) | 8,902-9,090 | Supports primary cleavage at RB-Like site |
| 17. Right Border (RB) sequence | Synthetic | AY566555 (bases 392-416) | 9,066-9,090 | Site for primary cleavage to release single stranded DNA insert from pSIM1278 (van Haaren et al. 1989) |

Example 5

The *Agrobacterium* Strain and Transfection

The C58-derived *Agrobacterium* strain AGL1 was developed by precisely deleting the transfer DNA of the hypervirulent plasmid, pTiBo542 (Lazo et al. 1991). Transformed plants were grown on media containing the antibiotic, timentin, which prevents survival of *Agrobacterium*, and thus selects for plants free of *Agrobacterium*. Following selection, plants are both antibiotic and *Agrobacterium* free, with the potato-derived expression cassettes inserted into the plant's genome.

Stock plants were maintained in magenta boxes with 40 ml half-strength M516 (Phytotechnology) medium containing 3% sucrose and 2 g/l gelzan (propagation medium). Potato internode segments of four to six mm were cut from four-week old plants, infected with the *Agrobacterium* AGL1 strain carrying pSIM1278, and transferred to tissue culture media containing 3% sucrose and 2 g/l gelzan (co-cultivation medium). Infected explants were transferred, after two days, to M404 (Phytotechnology) medium containing 3% sucrose, 2 g/l gelzan, 300 mg/l timentin and 1.2 ml plant protection medium (Phytotechnology) to eliminate *Agrobacterium* (hormone-free medium). Evidence that the plants were *Agrobacterium*-free was obtained by incubating stem and/or leaf fragments of transformed events on nutrient broth-yeast extract (NBY medium) for 2 weeks at 28° C. (repeated twice) with no outgrowth. Transformed plants were transported and planted in the field only when free of live *Agrobacterium*. Details of the methods are described elsewhere (Richael et al. 2008).

Although *Agrobacterium* is effective in cleaving at the Right Border (RB) site, it often fails to fully release the DNA insert from its plasmid vector by also cutting at the Left Border (LB) site (Gelvin 2003). Consequently, some infected plant cells received the DNA insert itself as well as additional plasmid backbone sequences containing the backbone marker gene, isopentenyltransferase (ipt), for a plant hormone cytokinin, which commonly regulates growth and development processes in plants. Overexpression results in stunted phenotypes, abnormal leaves, or the inability to root due to the cytokinin overproduction, which were used to select against plants containing backbone DNA (Richael et al. 2008). Every two weeks, the infected explants were transferred to fresh medium lacking any synthetic hormones and incubated in a Percival growth chamber under a 16-hr photoperiod at 24° C. where they started to form shoots. Many shoots expressed the ipt gene and displayed the cytokinin-overproduction phenotype; these shoots were discarded and not considered for further analyses. PCR genotyping demonstrated that about 0.3 to 1.5% of the remaining shoots contained at least part of the DNA insert while lacking the ipt gene.

The Russet Burbank W8 event contains inserts derived from two separate transformations with different plasmids. The first insert, plasmid pSIM1278, contains two cassettes consisting of inverted repeats designed to silence up to four potato genes, Asn1, Ppo5, R1, and PhL, in tubers. Similarly, the second plasmid, pSIM1678, contains a cassette consisting of an inverted repeat to silence the VInv gene in tubers, while also containing a copy of the Rpi-vnt1 gene under its native potato promoter.

Genetic and structural characterization of the inserts associated with transformation of Russet Burbank by pSIM1278 and pSIM1678 to produce event W8 showed that both transformations resulted in a single integration site for each plasmid. The structure of the DNA derived from transformation of pSIM1278 was complex relative to the structure of the original insert. The inserted DNA appears to have undergone rearrangement during transformation resulting in a structure consisting of a tandem repeat of the Asn1/Ppo5 silencing cassette, followed by a nearly complete pSIM1278 construct, and an inverted repeat containing a duplication of the pR1/pPh1 silencing cassette and a tandem duplication of the Gbss promoter with intervening Ph1 sequence.

Although this structure is more complicated than anticipated, the duplicated silencing cassettes are intact and remain under the control of the tissue-specific promoters. The structure does not negatively impact safety or trait efficacy of the product.

W8 also contains a single copy of the DNA from pSIM1678 that resides at a single locus of integration. The DNA insert of pSIM1678 contains a nearly intact DNA insert with a 330-bp deletion, which removes the entire T-DNA left border and 137-bp of the Rpi-vnt1 promoter. This small deletion in the promoter does not affect the gene's ability to confer late blight resistance. Also, RNA expression associated with the Rpi-vnt1 gene has been demonstrated using RT-PCR.

Example 6

Evidence for the Absence of the Vector Backbone DNA

The following methods were used to establish that backbone portions of the plasmid were not present in events developed for commercial purposes: 1) If plants had phenotypes associated with the negative selectable isopentenyl isomerase (ipt) marker gene in the plasmid backbone, they were discarded; 2) Absence of the backbone DNA was confirmed with Southern blot hybridization; 3) PCR was used to confirm no fragments of the backbone DNA were present. Collectively, Southern blot and PCR analyses have shown that the Russet Burbank W8 event does not contain backbone from either plasmid used in the transformations.

Example 7

Stability of the Inserted DNA

Bacterial T-DNAs are not always stable after insertion into a plant. The estimated instability rate ($0.5$-$5.9 \times 10^{-4}$) is associated with meiosis (Müller et al. 1987; Conner et al. 1998), which is not relevant to potatoes as they reproduce vegetatively. Thus, DNA insertions are expected to be stable. Tubers rather than seeds were used to define subsequent generations since tubers are what are commercially planted.

Genetic stability was assessed using both molecular and phenotypic assays. The structure of the insert was shown to be stable using Southern blot analysis of genomic DNA isolated over three generations of W8 potatoes (G0-G3), whereas the phenotypic stability was assessed by measuring polyphenol oxidase activity, in the second generation of field-grown tubers. This method shows visual evidence of PPO silencing after applying catechol to the cut surface of potatoes. These studies were carried out to ensure that the desired genetic changes in W8 remained stable over multiple clonal cycles while maintaining the traits.

The stability of the DNA inserts was evaluated by comparing three successive clonal generations (G1, G2, and G3) to the original transformant (G0) using Southern blots. Stable DNA inserts are expected to maintain the same structure and thus produce the same digestion patterns over multiple generations of the plant. To test stability of the inserts in the W8 event, its digestion pattern was compared using two probes (GBS1 and AGP) that hybridize to regions of the inserts from both pSIM1278 and pSIM1678, and two probes (INV and VNT1) that are specific to the pSIM1678 insert. Since the DNA sequences these probes hybridize with are contained in the potato genome as well as within the DNA insert(s), both endogenous and insert-specific bands are expected in the Southern blots.

All genomic DNA samples were digested with the restriction enzyme, EcoRV, and hybridized with a probe specific to either AGP or GBS1. EcoRV was chosen for these studies as it digests within both inserts to provide a unique banding pattern with internal bands of predicted size in the pSIM1278 insert (e.g. 2.3 kb). The banding patterns between all samples of W8 were identical to each other for both probes. The multiple bands present in the Russet Burbank control are also found in W8, but W8 also contains bands corresponding to the pSIM1278 and pSIM1678 inserts. These bands are similarly consistent between all generations of W8 analyzed indicating genetic stability of both inserts.

A second analysis was performed using two probes specific to the pSIM1678 insert. For this analysis, genomic DNA samples were digested with the restriction enzyme, XbaI, and hybridized with VNT1 and INV probes. XbaI was chosen as the restriction enzyme for these studies as it digests the pSIM1678 internally and produces a band of known size (e.g. 4.6 kb for the INV probe). Again, both endogenous and insert-specific bands were detected with consistent banding patterns between the three generations analyzed. The genetic and phenotypic analyses indicated the insertions arising from transformation of both pSIM1278 and pSIM1678 are stable over three generations. Given the demonstrated stability over three generations, it is likely that stability will be maintained during subsequent cycles of vegetative propagation.

Example 8

Efficacy and Tissue-Specificity of Gene Silencing

Figure 4:
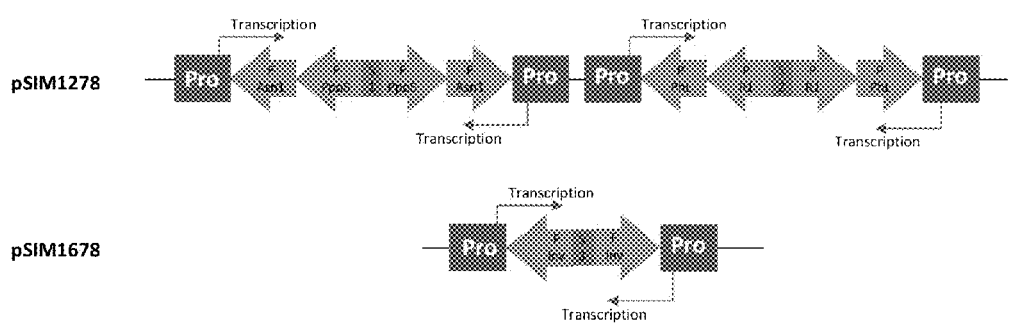
FIG. 4 provides a schematic representation of the silencing cassettes in the DNA insert inserted in the pSIM1278 transformation vector (upper construct) and the silencing cassette in the DNA insert inserted in the pSIM1678 transformation vector (lower construct).

Silencing was achieved by introducing inverted repeats containing sequences derived from the genes and promoters targeted for silencing. Although there are a number of parallel pathways involved in double-stranded RNA mediated silencing, transcription of these inverted repeats is thought to be processed by the cellular machinery involved in the viral defense (Fusaro et al. 2006). W8 potatoes contain three unique cassettes, which contain sequence from a total of five different potato genes. The pSIM1278 construct consists of two gene silencing cassettes (see FIG. 4, upper construct). One cassette contains an inverted repeat of sequence from two genes, asparagine synthetase-1 (Asn1) and polyphenol oxidase-5 (Ppo5). The second cassette includes sequence from the promoters of the starch associated genes, R1 (531-bp) and phosphorylase-L (PhL) (508-bp). The final cassette was introduced through the pSIM1678 construct, which includes an inverted repeat containing sequence from the vacuolar invertase (VInv) gene (see FIG. 4, lower construct).

All three silencing cassettes are regulated by the same set of well-characterized and tissue-specific promoters from the Agp and Gbss genes of potato, which are highly active in tubers compared with photosynthetically-active tissues and roots (Nakata et al. 1994; Visser et al. 1991). Therefore, expression and gene silencing was expected to be most effective in and largely limited to tubers.

Figure 5:
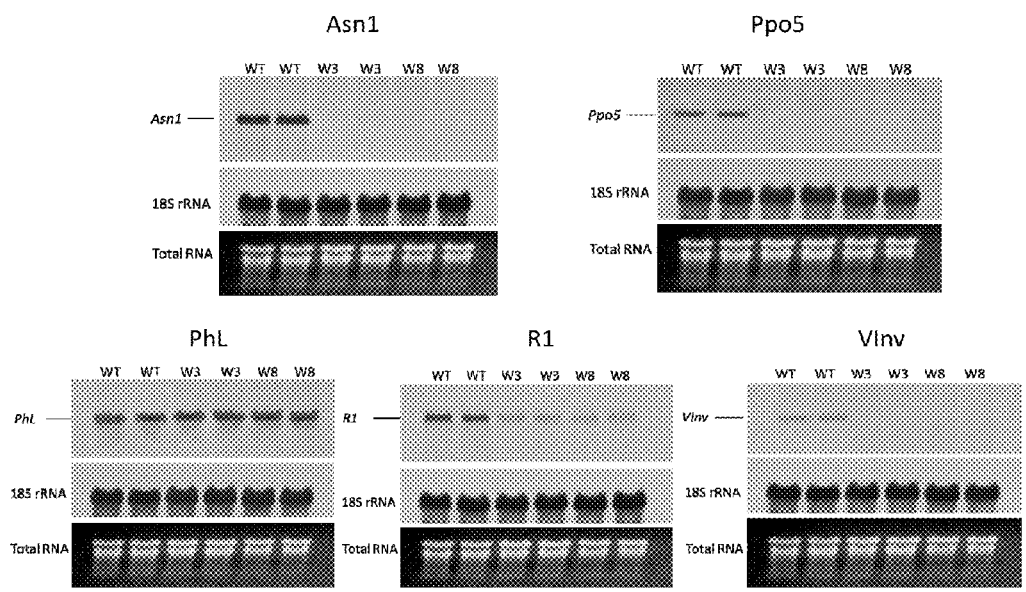
FIG. 5 shows the results of Northern blot analysis of total RNA (20 µg) isolated from tubers of field-grown plants for two events (W3 and W8) along with the Russet Burbank control (WT). Blots were hybridized with probes specific to the Asn1, Ppo5, PhL, R1, and VInv transcripts (upper panels). A probe specific to the internal control 18s rRNA (middle panels) and ethidium bromide stained total RNA (lower panels) were used as internal and loading controls. Each blot includes two independent biological replicates for each sample. W3=Additional event that was not submitted.

The expression of all five target genes was characterized by northern blot analysis to determine the effectiveness of gene silencing from each cassette. Robust silencing of Asn1, Ppo5, and VInv was observed in tubers while silencing of R1 was less effective (FIG. 5). Silencing of PhL was considered ineffective as no measurable differences between control and W8 samples were observed. In other events with the same pSIM1278 construct, partial silencing of the promoters for PhL and R1 in tubers was observed (Collinge and Clark 2013).

Previous studies have shown that Ppo gene silencing reduces the amount of associated protein to levels undetectable by western blot analysis (Llorente et al. 2011). Similarly, silencing of the R1 gene diminished accumulation of a ~160 kDa protein that is at least partially bound to starch granules (Lorberth et al. 1998).

Figure 6:
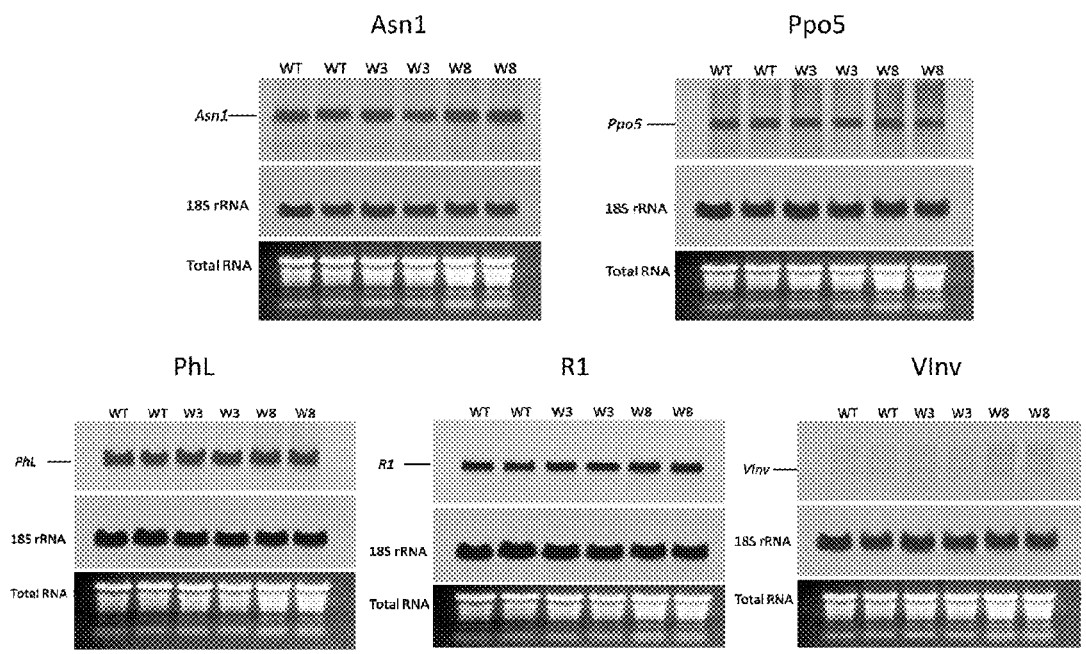
FIG. 6 shows the results of Northern blot analysis of total RNA (20 µg) isolated from leaves of field-grown plants for two events (W3 and W8) along with the Russet Burbank control (WT). Blots were hybridized with probes specific to the Asn1, Ppo5, PhL, R1, and VInv transcripts (upper panels). A probe specific to the internal control 18s rRNA (middle panels) and ethidium bromide stained total RNA (lower panels) were used as internal and loading controls. Each blot includes two independent biological replicates for each sample. W3=Additional event that was not submitted.
Figure 7:
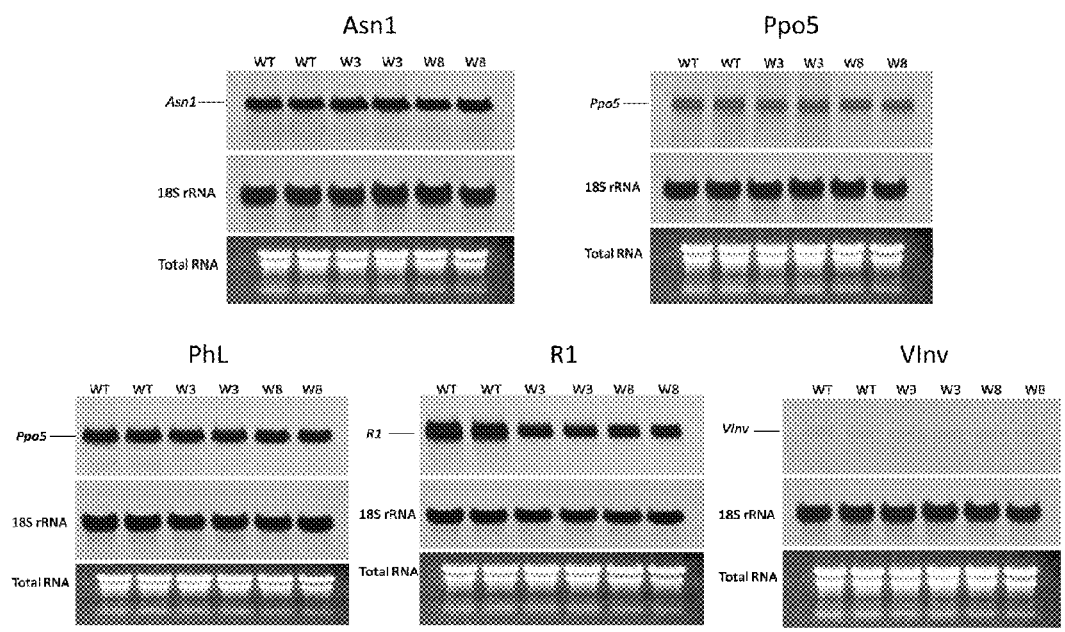
FIG. 7 shows the results of Northern blot analysis of total RNA (20 μg) isolated from stems of field-grown plants for two events (W3 and W8) along with the Russet Burbank control (WT). Blots were hybridized with probes specific to the Asn1, Ppo5, PhL, R1, and VInv transcripts (upper panels). A probe specific to the internal control 18s rRNA (middle panels) and ethidium bromide stained total RNA (lower panels) were used as internal and loading controls. Each blot includes two independent biological replicates for each sample. W3=Additional event that was not submitted.
Figure 8:
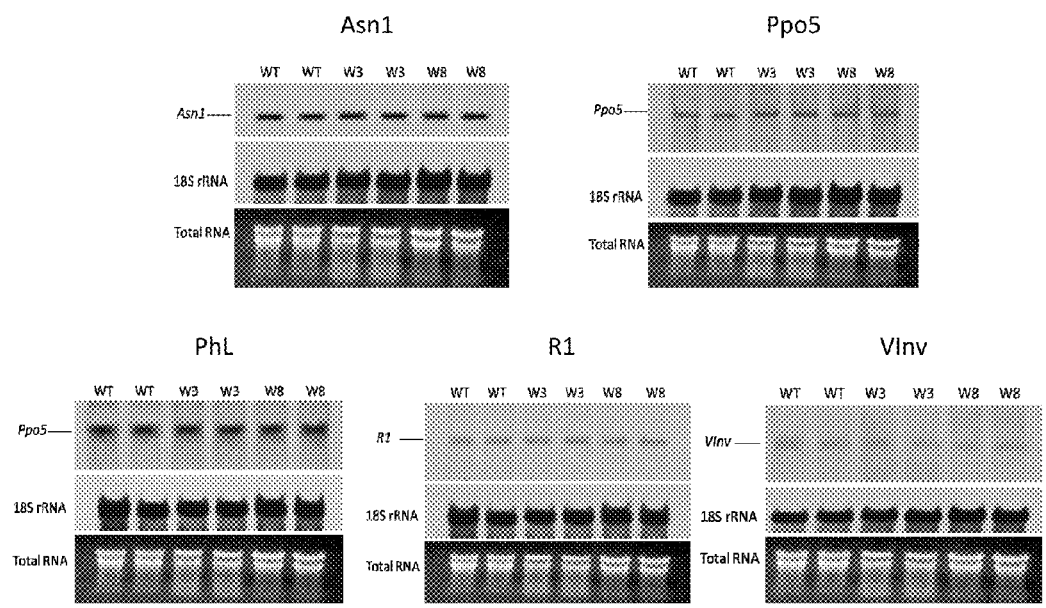
FIG. 8 shows the results of Northern blot analysis of total RNA (20 μg) isolated from roots of field-grown plants for two events (W3 and W8) along with the Russet Burbank control (WT). Blots were hybridized with probes specific to the Asn1, Ppo5, PhL, R1, and VInv transcripts (upper panels). A probe specific to the internal control 18s rRNA (middle panels) and ethidium bromide stained total RNA (lower panels) were used as internal and loading controls. Each blot includes two independent biological replicates for each sample. W3=Additional event that was not submitted.

Target gene expression was evaluated in other plant tissues to determine the specificity of the gene silencing. Northern blot analysis was similarly performed on RNA isolated from leaves, stems, roots, and flowers from W8 and the Russet Burbank control. As shown in FIGS. 6, 7 and 8 there was no silencing of target genes in leaves, stems, or roots relative to the Russet Burbank controls. All transcripts were readily detectable, except those corresponding to the VInv gene, which was weakly expressed in all leaf and stem samples, including controls.

Figure 9:
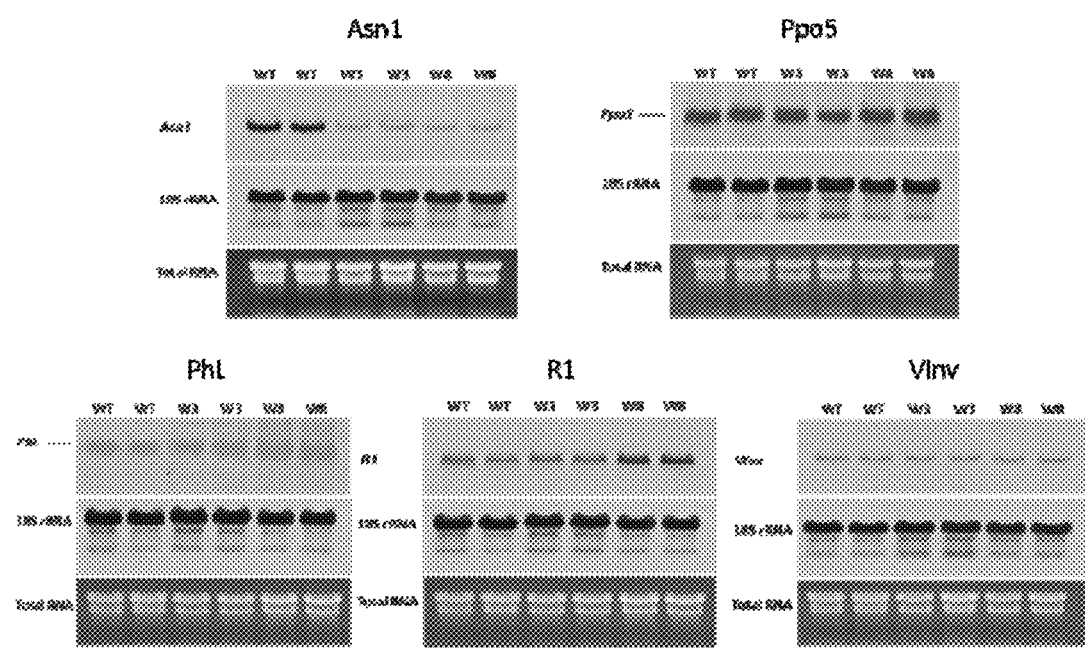
FIG. 9 shows the results of Northern blot analysis of total RNA (20 μg) isolated from flowers of field-grown plants for two events (W3 and W8) along with the Russet Burbank control (WT). Blots were hybridized with probes specific to the Asn1, Ppo5, PhL, R1, and VInv transcripts (upper panels). A probe specific to the internal control 18s rRNA (middle panels) and ethidium bromide stained total RNA (lower panels) were used as internal and loading controls. Each blot includes two independent biological replicates for each sample. W3=Additional event that was not submitted.

The only tissue other than tubers where some target silencing was observed was in the flower samples. These samples indicated some silencing of the Asn1 transcript in W8 relative to the Russet Burbank controls, which may be due to some leaky expression in that tissue (FIG. 9).

Two of the three gene silencing cassettes introduced into Russet Burbank to generate the W8 event were very effective at silencing their target transcripts for RNAi-mediated silencing. These two constructs effectively silenced Asn1, Ppo5, and VInv in the tubers of W8. The specificity of silencing to the tubers indicates that few, if any, of the siRNA generated by the RNAi machinery spread to other tissues or that their levels were insufficient to invoke an RNAi response in those tissues. The only evidence for silencing outside of tubers was in flowers where lower levels of Asn1 were observed, yet the magnitude of change was much lower than in tubers. The promoter silencing strategy with PhL and R1 had minimal effect, which was consistent with other events containing the same pSIM1278 construct (Collinge and Clark 2013).

As expected, the reduced expression of RNA transcripts associated with Asn1, Ppo5, and VInv were further corroborated. In addition, the compositional and agronomic data did not reveal any unexpected phenotypes that would be associated with significant off-target effects or unintended silencing. For instance, strong silencing of Asn1 in tubers limits the accumulation of the amino acid asparagine, whereas silencing of Asn1 in leaves or stems might adversely affect growth and development, which was not the case. Thus, the RNAi response was both effective and specific and there is no indication that silencing these potato genes would affect weediness or other plant-pest characteristics.

Example 9

Potato Cultivar W8 Characterization Summary

Potato variety W8 addresses the need of the potato industry to improve quality by increasing resistance to late blight, reducing expression of the enzyme responsible for black spot bruise and to reduce acrylamide through lowering the concentration of the reactants, namely asparagine and reducing sugars. Potato variety W8 was transformed with nucleic acid sequences that are native to the potato plant genome and does not contain foreign DNA, *Agrobacterium* DNA, viral markers or vector backbone sequences In addition, agronomic studies were conducted to ensure that the events grew the same as conventional controls, with the exception of the characteristics associated with the trait Agronomic Characterisics Agronomic trials were held to confirm that Russet Burbank variety W8 has an equivalent phenotype compared to the control Russet Burbank when grown at multiple locations representing the major areas for potato production in the U.S. Summaries of the evaluations of agronomic characteristics, yield and grading characteristics of W8 and controls grown in 2012 and 2013 are shown in Tables 4 and 5. Overall, the results confirm that there are no major differences between W8 and the control with respect to these characteristics. In Tables 4 and 5 below, column 1 shows the characteristic, column 2 shows the variety, column 3 shows the number of plants tested, column 4 shows the LS mean value for the characteristic, column 5 shows the p-value (bold and underlined indicate statistically significant differences), column 6 shows the standard deviation (SD), column 7 shows the 90% confidence interval (CI), and column 8 shows the range of mean values of conventional varieties (CVR). In Table 5, the color of fried tuber strips was compared to a USDA Munsell color chart. High sugar is the percentage of tubers with fry strips which, when compared with the Munsell Color Chart for french fried potatoes, has on the darkest side a predominate color of a number 3 or darker. Sugar ends is the percentage of tubers with fry strips which have an end ¼inch long or longer on the darkest side of the strip for the full width of the strip, testing number 3 or darker color (USDA AMS 1969). Fry 0-Fry 4 is the percent of tubers with fry strips which, when the predominate color of the darkest side is compared with the Munsell Color Chart for french fried potatoes, is determined to be a color reading of 0-4, respectively. Therefore, the reported numbers are the percentage of Fries that score 0, 1, 2, 3, or 4 on the Munsell chart. The lower the color the better, 0 is the best.

TABLE 4

| Characteristic | Variety | N | Mean | P-Value | SD | 90% CI | | CVR | |
|---|---|---|---|---|---|---|---|---|---|
| Early Emergence (%) | Control | 41 | 61.5 | . | 14.8 | 57.1 | 64.9 | 0.0 | 93.1 |
| | W8 | 40 | 39.5 | 0.0001 | 23.3 | 31.8 | 44.3 | | |
| Final Emergence (%) | Control | 41 | 87.1 | . | 10.7 | 84.4 | 90.0 | 10.6 | 98.1 |
| | W8 | 40 | 80.3 | 0.2060 | 20.2 | 74.4 | 85.1 | | |
| Stems Per Plant (#) | Control | 39 | 1.7 | . | 0.7 | 1.4 | 1.8 | 1.0 | 3.1 |
| | W8 | 36 | 1.7 | 0.8868 | 0.7 | 1.4 | 1.8 | | |
| Plant Vigor (1-5 Scale) | Control | 37 | 3.7 | . | 0.9 | 3.4 | 3.9 | 2.0 | 5.0 |
| | W8 | 35 | 3.0 | 0.0065 | 0.8 | 2.8 | 3.2 | | |
| Plant Height (cm) | Control | 41 | 45.1 | . | 14.0 | 42.7 | 50.0 | 31.8 | 71.6 |
| | W8 | 38 | 40.4 | 0.0098 | 12.5 | 38.0 | 44.9 | | |
| Vine Desiccation (%) | Control | 37 | 44.0 | . | 29.3 | 37.0 | 53.3 | 3.8 | 100.0 |
| | W8 | 35 | 35.5 | 0.1471 | 30.7 | 29.4 | 46.9 | | |

TABLE 5

| Characteristic | Variety | N | Mean | P-Value | SD | 90% CI | | CVR | |
|---|---|---|---|---|---|---|---|---|---|
| Total Yield (cwt/a) | Control | 41 | 445.7 | . | 149.7 | 397.1 | 475.9 | 135.6 | 733.2 |
| | W8 | 38 | 417.9 | 0.4080 | 165.4 | 360.8 | 451.3 | | |
| US#2 Yield (cwt/a) | Control | 41 | 375.7 | . | 147.5 | 328.8 | 406.3 | 118.9 | 653.7 |
| | W8 | 38 | 312.2 | 0.0506 | 144.1 | 264.2 | 343.1 | | |
| Tubers Per Plant (#) | Control | 41 | 7.8 | . | 2.5 | 7.0 | 8.3 | 2.5 | 19.5 |
| | W8 | 38 | 8.4 | 0.4657 | 3.2 | 7.2 | 8.9 | | |
| Tubers <4 oz (%) | Control | 9 | 8.2 | . | 5.3 | 4.9 | 11.5 | . | . |
| | W8 | 9 | 15.9 | 0.2434 | 6.9 | 11.7 | 20.2 | | |
| Tubers 4-6 oz (%) | Control | 41 | 18.5 | . | 8.6 | 16.5 | 21.0 | 4.6 | 41.1 |
| | W8 | 41 | 20.5 | 0.3148 | 7.1 | 18.8 | 22.6 | | |
| Tubers 6-10 oz (%) | Control | 41 | 31.1 | . | 8.7 | 28.9 | 33.5 | 15.3 | 41.2 |
| | W8 | 41 | 28.6 | 0.3435 | 8.2 | 26.1 | 30.5 | | |
| Tubers 10-14 oz (%) | Control | 41 | 19.0 | . | 8.4 | 16.7 | 21.1 | 1.0 | 26.8 |
| | W8 | 41 | 14.0 | 0.0071 | 8.1 | 11.8 | 16.0 | | |
| Tubers >14 oz (%) | Control | 41 | 14.3 | . | 16.9 | 9.3 | 18.2 | 0.0 | 45.5 |
| | W8 | 41 | 8.6 | 0.0554 | 11.0 | 5.8 | 11.5 | | |
| Specific Gravity | Control | 41 | 1.077 | . | 0.0 | 1.1 | 1.1 | 0.7 | 1.2 |
| | W8 | 41 | 1.073 | 0.8058 | 0.0 | 1.1 | 1.1 | | |
| High Sugar (%) | Control | 41 | 11.0 | . | 16.9 | 6.0 | 14.9 | 0.0 | 84.8 |
| | W8 | 41 | 1.4 | 0.0337 | 7.3 | 0 | 3.4 | | |
| Sugar Ends (%) | Control | 41 | 19.7 | . | 18.5 | 14.7 | 24.4 | 0.0 | 52.6 |
| | W8 | 41 | 3.3 | <.0001 | 6.5 | 1.2 | 4.6 | | |
| Fry 0 | Control | 32 | 76.5 | . | 30.9 | 67.2 | 85.7 | 0.0 | 100.0 |
| | W8 | 32 | 94.9 | 0.0272 | 19.4 | 89.1 | 100.0 | | |
| Fry 1 | Control | 32 | 2.9 | . | 10.5 | 0.0 | 6.0 | 0.0 | 29.7 |
| | W8 | 32 | 1.5 | 0.6142 | 6.2 | 0.0 | 3.4 | | |
| Fry 2 | Control | 32 | 9.9 | . | 18.9 | 4.3 | 15.6 | 0.0 | 28.4 |
| | W8 | 32 | 1.7 | 0.0173 | 7.3 | 0.0 | 3.9 | | |
| Fry 3 | Control | 32 | 1.9 | . | 3.7 | 0.8 | 3.0 | 0.0 | 23.1 |
| | W8 | 32 | 0.8 | 0.4899 | 3.4 | 0.0 | 1.8 | | |
| Fry 4 | Control | 32 | 6.3 | . | 14.8 | 1.8 | 10.7 | 0.0 | 79.7 |
| | W8 | 32 | 1.0 | 0.2316 | 5.9 | 0.0 | 2.8 | | |
| Total Internal Defects (%) | Control | 41 | 1.6 | . | 2.5 | 0.8 | 2.1 | 0.0 | 15.5 |
| | W8 | 41 | 1.2 | 0.7205 | 2.2 | 0.6 | 1.8 | | |

Based on the data presented in Tables 4 and 5 for potato cultivar W8, it can be concluded that overall there are no major differences in agronomic characteristics, yield and grading, and ecological interactions between the untransformed Russet Burbank variety and potato cultivar W8, with the exception of early emergence percent and sugar ends percent. Therefore, based on the multi-year data, the Russet Burbank variety W8 poses no significant risk of persistence in the environment as a result of weediness or plant pest potential.

Late Blight Resistance

Many potato cultivars are susceptible to late blight, a devastating disease caused by the fungus-like oomycete pathogen *Phytophthora infestans*. Late blight of potato is identified by black/brown lesions on leaves and stems that may expand rapidly and become necrotic. Severe late blight epidemics occur when *P. infestans* grows and reproduces rapidly on the host crop.

The potato late blight resistance gene known as Rpi-vnt1 has been added to W8, successfully conferring late blight resistance. To demonstrate the efficacy of late blight resistance, studies were conducted by inoculating both foliage and tubers of Russet Burbank variety W8 and a control Russet Burbank.

At the end of the trial period, the rating from each site was taken and is summarized in Tables 6 and 7 below. The results of the foliar resistance to potato late blight are shown in Table 6. Each strain site had different strain inoculum that included US-8, US-22 or US-23, depending on the strains that were found in that area. Table 6, column 1 shows the variety, column 2 shows the LS mean percent foliar late blight infection, column 3 shows the p-value, where significant differences between W8 and the control are in bold and underlined, and column 4 shows the conventional variety range, which is the range of mean values of conventional varieties.

TABLE 6

| Variety | Mean Percent Foliar Late Blight Infection | P-value | CVR |
|---|---|---|---|
| Control | 58.3 | <u><.0001</u> | 18.8-100 |
| W8 | 0.50 | . | . |

As shown in Table 6, a significant reduction in percent foliar late blight infection was detected for W8 compared to the Russet Burbank control, which supports the conclusion that the potato late blight resistance gene confers resistance to late blight in W8 and is efficacious in the foliage.

Table 7 below shows the results of tuber late blight infection rate of W8 and the control as determined by percent infection. Table 7, column 1 shows the late blight isolate, column 2 shows the variety, column 3 shows the mean percent late blight tuber infection and column 4 shows the P-value, where significant differences between W8 and the control Russet Burbank are in bold and underlined.

TABLE 7

| Isolate | Variety | Mean Percent Late Blight Tuber Infection | P-value |
|---|---|---|---|
| US-22 | Control | 100.0 | . |
| US-22 | W8 | 51.0 | <u><0.0001</u> |
| US-8 | Control | 67.0 | . |
| US-8 | W8 | 21.1 | <u><0.0001</u> |

As shown in Table 7, a significant reduction in percent late blight infection in tubers was detected for W8 compared to the control for both US-22 and US-8 isolates.

Black Spot Bruise Tolerance

Black spot bruise is a discoloration affecting bruised tubers that represents one of the most important quality issues for the potato industry. The condition is a result of leakage of polyphenol oxidase (Ppo) from damaged plastids into the cytoplasm. In the cytoplasm, the enzyme oxidizes polyphenol, which then form dark precipitants. One of the two silencing cassettes of the pSIM1278 DNA insert contains two copies of a fragment of the Ppo5 gene from *Solanum verrucosum* positioned as inverted repeat between regulatory elements. Expression of this inverted repeat triggers silencing of the potato Ppo5 gene and significantly reduces the incidence of black spot bruise.

Tubers of potato cultivar W8 and a control Russet Burbank variety, which is susceptible to black spot bruise, were assayed in two ways for black spot bruise tolerance.

Figure 10:
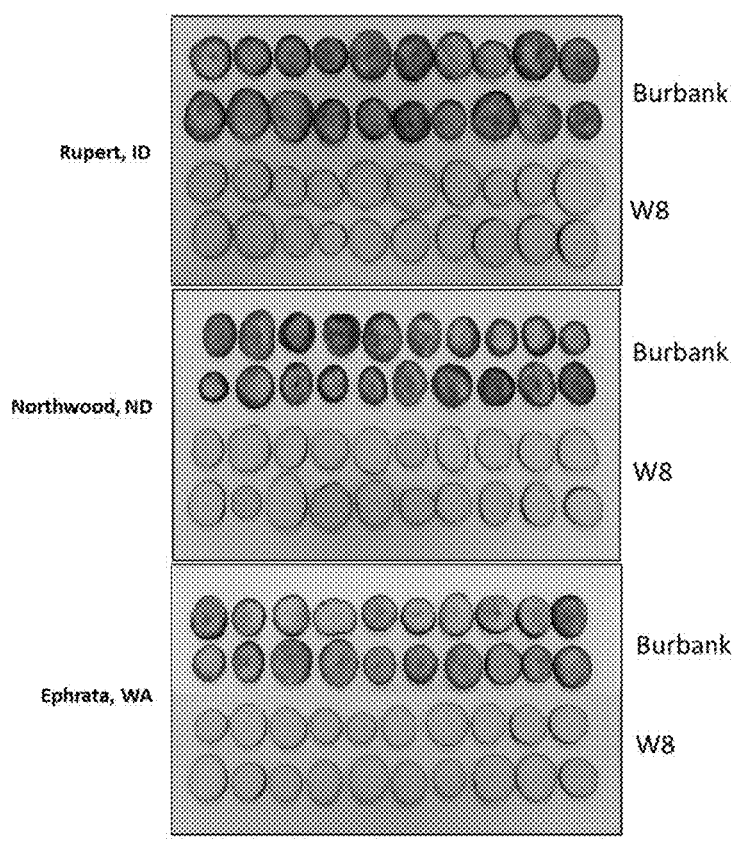
FIG. 10 shows the results of three different catechol assays for polyphenol oxidase activity. For each assay, the Russet Burbank control is on the top and variety W8 is on the bottom. Dark brown indicates that the trait for black spot bruise reduction is not present.

Tuber discoloration is caused by the activity of polyphenol oxidase, which oxidizes phenols including catechol to produce compounds that rapidly polymerize to produce pigments. An indirect method to test for black spot bruise tolerance is based on pipetting 1-ml catechol (25 mM in 50 mM MOPS, pH6.5) onto the cut surfaces of tubers and monitoring for the Ppo-dependent development of a dark brown precipitate. The Ppo-dependent development of a dark brown precipitate was assessed after 20 min. The results of the catechol assay for potato cultivar W8 are shown in FIG. 10. As seen in FIG. 10, the Russet Burbank control turned dark brown indicating black spot bruise, whereas potato cultivar W8 did not turn dark brown indicating that W8 is more resistant to black spot bruise than the untransformed Russet Burbank control, and supporting the efficacy of the reduced black spot trait.

The second method of assaying for bruise tolerance was by measuring PPO activity with an enzymatic assay. Conversion of L-DOPA to dopachrome was monitored over time by measuring $A_{474nm} \cdot \Delta A_{474nm} \cdot min^{-1}$, which was converted to units of $\mu mol \cdot min^{-1} \cdot mg\ dw\ tuber^{-1}$. As shown in Table 8, the enzymatic assay shows that W8 has a 90% decrease in PPO activity (0.025 $\mu mol \cdot min^{-1} \cdot mg\ dw\ tuber^{-1}$) when compared to the Russet Burbank control. The reduced activity in W8 tubers was associated with reduced black spot through silencing of the Ppo5 gene.

TABLE 8

| Variety | PPO activity ($\mu mol \cdot min^{-1} \cdot mg\ dw\ tuber^{-1}$) |
|---|---|
| Russet Burbank W8 | 0.0018 |
| Russet Burbank control | 0.0258 |

Asparagine and Acrylamide Levels

Tubers of potato cultivar W8 contained less free asparagine, but more aspartic acid, glutamine and glutamic acid than the control at harvest, as shown in Table 9. The mean values of free asparagine, aspartic acid, glutamine and glutamic acid for W8 were all within the tolerance intervals and combined literature ranges, and therefore considered within the normal range for potatoes. Table 9, column 1 shows the amino acid in mg/100 g, column 2 shows the variety, column 3 shows the LS mean, column 4 shows the P-value, where significant differences between W8 and the control Russet Burbank are in bold and underlined, column 5 shows the number of plants tested, column 6 shows the range, column 7 shows the tolerance interval range (TI), column 8 shows the combined literature range (CLR), taken from Davies (1977), Shepherd et al. (2010) and Lisinska and Leszczynski (1989).

TABLE 9

| Compound | Variety | Mean | P-value | N | Range Min | Range Max | TI Min | TI Max | CLR Min | CLR Max |
|---|---|---|---|---|---|---|---|---|---|---|
| Asparagine (mg/100 g) | W8 | 87.8 | <.0001 | 41 | 62.1 | 140 | . | . | . | . |
| | Burbank | 300 | . | 41 | 198 | 469 | 60.0 | 482 | 31.2 | 698 |
| Aspartic Acid (mg/100 g) | W8 | 45.2 | 0.0032 | 41 | 32.8 | 63.9 | . | . | . | . |
| | Burbank | 40.4 | . | 41 | 27.9 | 52.7 | 12.6 | 72.8 | 6.4 | 75.2 |
| Glutamine (mg/100 g) | W8 | 252 | <.0001 | 41 | 203 | 335 | . | . | . | . |
| | Burbank | 139 | . | 41 | 95.7 | 198 | 23.3 | 260 | 44.0 | 540 |
| Glutamic Acid (mg/100 g) | W8 | 51.3 | <.0001 | 41 | 27.9 | 75.5 | . | . | . | . |
| | Burbank | 40.8 | . | 41 | 26.0 | 72.0 | 10.2 | 80.3 | 45.0 | 74.2 |

Lowered asparagine, fructose and glucose levels lead to an overall reduction of acrylamide in processed potato products because they are reactants in the formation of acrylamide. In order to demonstrate the efficacy of reducing acrylamide, field-grown tubers of W8 and the control Russet Burbank were analyzed at harvest and after storage for 3, 6 and 9 months at normal (46° F.) and cold (38° F.) storage temperatures, with the results shown in Tables 10 and 11. Before testing for acrylamide, W8 and the control Russet Burbank were made into French fries. Table 10 shows the French fry acrylamide levels in parts per billion (ppb) at harvest and after storage at 46° F. and Table 11 shows the French fry acrylamide levels in parts per billion (ppb) at harvest and after storage at 38° F. Tables 10 and 11, column 1 shows the timing of when the testing occurred, column 2 shows the compound, column 3 shows the variety, column 4 shows the LS mean acrylamide level in ppb, column 5 shows the P-value, where significant differences between W8 and the control are shown in bold and underlined, column 6 shows the percent reduction of acrylamide compared to the control at the same storage time, column 7 shows the number of tubers tested, column 8 shows the range of acrylamide in ppb, and column 9 shows the tolerance interval (TI).

sucrose to reducing sugars (glucose and fructose). Although silencing of R1 and PhL resulted in lowered levels of reducing sugar when analyzed at one month after harvest (Collinge and Clark 2013), the major reduction in reducing sugar appears to be related to invertase silencing. Overall benefits of silencing R1, PhL, and VInv include improved quality, especially relating to color control, and thus contributing to the desired golden brown colors required by most french fry or chip customers. Also, the reducing sugars react with amino acids, such as asparagine, to produce Maillard products including acrylamide.

The VInv gene silencing cassette in pSIM1678 results in decreased levels of vacuolar invertase, an enzyme which converts sucrose into glucose and fructose. When levels of invertase are decreased in potatoes, reducing sugars glucose and fructose remain at low levels during storage while sucrose increases, especially when held below typical storage temperatures of 46-48° F. for french fry potatoes. Before testing for invertase activity, tubers were stored at 39° F. for one month. Three replicates for each of W8 and Russet Burbank control were used for the assay and activity was measured by the accumulation of glucose in units of nmol/min/gm tuber. As shown in Table 12, W8 had an 85% reduction in vacuolar

TABLE 10

| Timing | Compound | Variety | Mean (ppb) | P-value | Percent Reduction | N | Range (ppb) Min | Range (ppb) Max | TI (ppb) Min | TI (ppb) Max |
|---|---|---|---|---|---|---|---|---|---|---|
| Fresh | Acrylamide | W8 | 75.3 | <.0001 | 85.0 | 41 | 32.7 | 185 | 10.0 | 1035 |
|  |  | Burbank | 503 | . | . | 41 | 229 | 971 |  |  |
| Month 3 at 46° F. | Acrylamide | W8 | 86.1 | <.0001 | 80.9 | 9 | 74.5 | 94.3 | 10.0 | 599 |
|  |  | Burbank | 450 | . | . | 9 | 393 | 514 |  |  |
| Month 6 at 46° F. | Acrylamide | W8 | 68.3 | 0.0011 | 83.7 | 9 | 50.4 | 96.2 | 10.0 | 688 |
|  |  | Burbank | 420 | . | . | 9 | 330 | 528 |  |  |
| Month 9 at 46° F. | Acrylamide | W8 | 115 | 0.0013 | 78.2 | 9 | 90.7 | 156 | 10.0 | 1047 |
|  |  | Burbank | 528 | . | . | 9 | 429 | 740 |  |  |

TABLE 11

| Timing | Compound | Variety | Mean (ppb) | P-value | Percent Reduction | N | Range (ppb) Min | Range (ppb) Max | TI (ppb) Min | TI (ppb) Max |
|---|---|---|---|---|---|---|---|---|---|---|
| Month 6 at 38° F. | Acrylamide | W8 | 203 | <.0001 | 86.2 | 3 | 199 | 207 | 1155 | 1792 |
|  |  | Burbank | 1473 | . | . | 3 | 1450 | 1500 |  |  |
| Month 9 at 38° F. | Acrylamide | W8 | 212 | <.0001 | 90.8 | 3 | 201 | 234 | 761 | 3839 |
|  |  | Burbank | 2300 | . | . | 3 | 2160 | 2380 |  |  |

As shown in Table 10, at the time of harvest, French fries made with W8 tubers contained 85% less acrylamide than the control Russet Burbank. When potatoes were stored throughout nine months at 46° F., acrylamide levels in W8 were 78% to 83.7% lower than the control Russet Burbank. As shown in Table 11, acrylamide levels in W8 French fries after storage at 38° F. for 6 to 9 months were consistently much lower than the controls.

Reducing Sugars and Invertase Silencing

Potato cultivar W8 contains expression cassettes that could lower levels of reducing sugars in tubers by multiple mechanisms. Through the transformation with pSIM1278, a silencing cassette for the promoters of the starch associated gene (R1) and the phosphorylase-L gene (PhL) were introduced, whereas transformation with pSIM1678 introduced a silencing cassette for the invertase gene (Ye et al. 2010). Together, these traits function by slowing the conversion of starch and invertase activity in cold-stored tubers compared to the control Russet Burbank. The reduced vacuolar invertase activity in W8 tubers is associated with reduced RNA accumulation from the VInv gene and lower levels of reducing sugars glucose and fructose, as shown in Tables 13 and 14.

TABLE 12

| Variety | Invertase activity (nmole glu/min/mg tuber) | Percent reduction |
|---|---|---|
| Russet Burbank W8 | 1.37 | 85% |
| Russet Burbank Control | 8.86 |  |

Long-term cold storage is necessary to maintain an adequate supply of high quality potatoes for year-round processing into french fries and potato chips, but also leads to cold-induced sweetening (CIS). CIS causes unwanted side effects in potato products processed at high temperatures including flavor changes, unwanted dark colors and elevated amounts of acrylamide. Vacuolar acid invertase (VInv) is an enzyme that is critically important in the CIS process in increasing the amount of glucose and fructose in tubers stored at very low temperatures (Zrenner et al. 1996). W8 has suppressed expression of the VInv gene and therefore has reduced glucose and fructose levels in cold storage and less CIS compared to the Russet Burbank control. In order to demonstrate efficacy of the traits leading to lowered reducing sugar, field-grown tubers of W8 and the untransformed control were analyzed at harvest and at normal (46° F.) and cold (38° F.) storage temperatures.

Reducing sugars, glucose plus fructose, and the non-reducing sugar, sucrose, were tested in W8 at the time of harvest and then after 3, 6, and 9 months of storage. Two different storage temperatures were used, 46° F., which is typically used for Russet Burbank potatoes destined for frozen french fries, and 38° F., a lower temperature enabled by silencing VInv, possibly allowing for better quality without high levels of reducing sugars. At harvest and all storage time points and temperatures, W8 tubers contained lower levels of reducing sugars fructose and glucose compared with the control, as shown in Tables 13 and 14. All sugar values for W8 at the time of harvest were within the tolerance interval, indicating compositional equivalence to the controls. Table 13 shows the potato sugar levels for fructose plus glucose and sucrose at harvest and after storage for 3, 6 or 9 months at 46° F. and Table 14 shows the potato sugar levels for fructose plus glucose and sucrose when stored for 6 or 9 months at 38° F. Tables 13 and 14, column 1 shows the timing of when the testing occurred, column 2 shows the variety, column 3 shows the LS mean sugar level in mg/100 g, column 4 shows the P-value, where significant differences between W8 and the control are shown in bold and underlined, column 5 shows the number of tubers tested, column 6 shows the range of sugars in mg/100 g, and column 7 shows the tolerance interval (TI).

TABLE 13

| Timing | Variety | Mean | P-value | N | Range Min | Range Max | TI Min | TI Max |
|---|---|---|---|---|---|---|---|---|
| Fructose + Glucose (mg/100 g) | | | | | | | | |
| Fresh | W8 | 38.4 | 0.0002 | 41 | 9.68 | 106 | 1.00 | 424 |
| | Control | 146 | . | 41 | 14.0 | 406 | | |
| Month 3 at 46° F. | W8 | 122 | 0.0056 | 9 | 54.1 | 210 | 1.00 | 996 |
| | Control | 483 | . | 9 | 298 | 598 | | |
| Month 6 at 46° F. | W8 | 116 | <.0001 | 9 | 20.8 | 310 | 1.00 | 640 |
| | Control | 261 | . | 9 | 153 | 459 | | |
| Month 9 at 46° F. | W8 | 106 | 0.032 | 9 | 79.7 | 160 | 1.00 | 648 |
| | Control | 224 | . | 9 | 105 | 372 | | |
| Sucrose (mg/100 g) | | | | | | | | |
| Fresh | W8 | 395 | <.0001 | 41 | 161 | 775 | 1.00 | 512 |
| | Control | 241 | . | 41 | 113 | 558 | | |
| Month 3 at 46° F. | W8 | 651 | <.0001 | 9 | 520 | 738 | 1.00 | 1125 |
| | Control | 148 | . | 9 | 56.2 | 228 | | |

TABLE 13-continued

| Timing | Variety | Mean | P-value | N | Range Min | Range Max | TI Min | TI Max |
|---|---|---|---|---|---|---|---|---|
| Month 6 at 46° F. | W8 | 202 | 0.0021 | 9 | 177 | 229 | 1.00 | 345 |
| | Control | 97.6 | . | 9 | 80.1 | 144 | | |
| Month 9 at 46° F. | W8 | 146 | <.0001 | 9 | 105 | 201 | 10.4 | 103 |
| | Control | 56.9 | . | 9 | 44.8 | 77.3 | | |

TABLE 14

| Timing | Variety | Mean | P-value | N | Range Min | Range Max | TI Min | TI Max |
|---|---|---|---|---|---|---|---|---|
| Fructose + Glucose (mg/100 g) | | | | | | | | |
| Month 6 at 38° F. | W8 | 91.7 | 0.0002 | 3 | 83.7 | 97.4 | 1.00 | 1586 |
| | Control | 640 | . | 3 | 590 | 726 | | |
| Month 9 at 38° F. | W8 | 151 | <.0001 | 3 | 102 | 188 | 183 | 1586 |
| | Control | 754 | . | 3 | 703 | 788 | | |
| Sucrose (mg/100 g) | | | | | | | | |
| Month 6 at 38° F. | W8 | 963 | <.0001 | 3 | 945 | 986 | 1.00 | 661 |
| | Burbank | 182 | . | 3 | 138 | 206 | | |
| Month 9 at 38° F. | W8 | 645 | <.0001 | 3 | 598 | 714 | 1.00 | 325 |
| | Burbank | 152 | . | 3 | 137 | 163 | | |

As shown in Tables 13 and 14, all W8 tubers contained more sucrose than control samples at harvest and after multiple storage time points at both 38° F. and 46° F. The net result of silencing the VInv gene in W8 is lower levels of reducing sugars and higher levels of sucrose. These changes are observed at the time of harvest and throughout the storage period of up to 9 months. Reducing sugars in W8 increase with storage time, but remain consistently lower than the Russet Burbank control. Much lower levels of reducing sugars were observed in W8 compared with controls when stored at 38° F., suggesting that lower temperature storage are feasible for W8. In all cases significant decreases in reducing sugars are coupled with higher levels of sucrose. It would be expected that lower temperature storage results in less shrink from respiration, but also would reduce losses from disease.

Russet Burbank potato cultivar W8 addresses the need of the potato industry to improve quality by having increased resistance to late blight, reduced expression of the enzyme responsible for black spot, reduced acrylamide through reduced asparagine and lowered levels of reducing sugars.

Further Embodiments of the Invention

The research leading to potato varieties which combine the advantageous characteristics referred to above is largely empirical. This research requires large investments of time, labor, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses and tubers are harvested and retained from thousands of individual seedlings. The next year one to four tubers from each resulting seedling are planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed potato plants, using transformation methods as described below to incorporate transgenes into the genetic material of the potato plant(s).

Traditional plant breeding typically relies on the random recombination of plant chromosomes to create varieties that have new and improved characteristics. According to standard, well-known techniques, genetic "expression cassettes," comprising genes and regulatory elements, are inserted within the borders of *Agrobacterium*-isolated transfer DNAs ("T-DNAs") and integrated into plant genomes. *Agrobacterium*-mediated transfer of T-DNA material typically comprises the following standard procedures: (1) in vitro recombination of genetic elements, at least one of which is of foreign origin, to produce an expression cassette for selection of transformation, (2) insertion of this expression cassette, often together with at least one other expression cassette containing foreign DNA, into a T-DNA region of a binary vector, which usually consists of several hundreds of basepairs of *Agrobacterium* DNA flanked by T-DNA border sequences, (3) transfer of the sequences located between the T-DNA borders, often accompanied with some or all of the additional binary vector sequences from *Agrobacterium* to the plant cell, and (4) selection of stably transformed plant cells that display a desired trait, such as an increase in yield, improved vigor, enhanced resistance to diseases and insects, or greater ability to survive under stress.

Thus, genetic engineering methods rely on the introduction of foreign, not-indigenous nucleic acids, including regulatory elements such as promoters and terminators, and genes that are involved in the expression of a new trait or function as markers for identification and selection of transformants, from viruses, bacteria and plants. Marker genes are typically derived from bacterial sources and confer antibiotic or herbicide resistance. Classical breeding methods are laborious and time-consuming, and new varieties typically display only relatively modest improvements.

In the "anti-sense" technology, the sequence of native genes is inverted to silence the expression of the gene in transgenic plants. However, the inverted DNA usually contains new and uncharacterized open reading frames inserted between the promoter and the terminator that encode foreign amino acid sequences that may be undesirable as they interfere with plant development and/or reduce their nutritional value.

Expression Vectors for Potato Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or bromoxynil. Comai et al., Nature 317:741-744 (1985), Gordon-Kamm et al., Plant Cell 2:603-618 (1990) and Stalker et al., Science 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984).

In vivo methods for visualizing GUS activity that do not require destruction of plant tissue are available. Molecular Probes publication 2908, IMAGENE GREEN, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263: 802 (1994). GFP and mutants of GFP may be used as screenable markers.

Expression Vectors for Potato Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters

An inducible promoter is operably linked to a gene for expression in potato. Optionally, the inducible promoter is operably linked to a nucleotide sequence encoding a signal sequence which is operably linked to a gene for expression in potato. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. USA 88:0421 (1991).

B. Constitutive Promoters

A constitutive promoter is operably linked to a gene for expression in potato or the constitutive promoter is operably linked to a nucleotide sequence encoding a signal sequence which is operably linked to a gene for expression in potato.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

C. Tissue-Specific or Tissue-Preferred Promoters

A tissue-specific promoter is operably linked to a gene for expression in potato. Optionally, the tissue-specific promoter is operably linked to a nucleotide sequence encoding a signal sequence which is operably linked to a gene for expression in potato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a potato plant. In another preferred embodiment, the biomass of interest is seed or tubers. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene(s) to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al. Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., Plant Molec. Biol. 24:25 (1994), who disclose the nucleotide sequences of several Clivia miniata mannose-binding lectin genes.

E. A vitamin-binding protein such as avidin. See PCT application US 93/06487 which teaches the use of avidin and avidin homologs as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776, which discloses peptide derivatives of Tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S. Current Biology, 5(2) (1995).

U. Antifungal genes. See Cornelissen and Melchers, Plant Physiol., 101:709-712 (1993); Parijs et al., Planta 183:258-264 (1991) and Bushnell et al., Can. J. of Plant Path. 20(2): 137-149 (1998).

V. Genes that confer resistance to *Phytophthora* blight, such as the R1, R2, R3, R4 and other resistance genes. See, Naess, S. K., et. al., (2000) Resistance to late blight in *Solanum bulbocastanum* is mapped to chromosome 8. Theor. Appl. Genet. 101: 697-704 and Li, X., et. al., (1998) Autotetraploids and genetic mapping using common AFLP markers: the R2 allele conferring resistance to *Phytophthora infestans* mapped on potato chromosome 4. Theor. Appl. Genet. 96: 1121-1128.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767, 373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, for example, this could be accomplished by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Potato Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation collectively referred to as direct gene transfer have been developed as an alternative to *Agrobacterium*-mediated transformation. A generally applicable method of plant surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of potato target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular potato line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Persons of ordinary skill in the art will recognize that when the term potato plant is used in the context of the present invention, this also includes derivative varieties that retain the essential distinguishing characteristics of W8, such as a gene converted plant of that variety or a transgenic derivative having one or more value-added genes incorporated therein (such as herbicide or pest resistance). Backcrossing methods can be used with the present invention to improve or introduce a characteristic into the variety. The term "backcrossing" as used herein refers to the repeated crossing 1, 2, 3, 4, 5, 6, 7, 8, 9 or more times of a hybrid progeny back to the recurrent parents. The parental potato plant which contributes the gene(s) for the one or more desired characteristics is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the one or more genes transferred from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety are modified, substituted or supplemented with the desired gene(s) from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In *Molecular Form and Function of the Plant Genome*, L. van Vloten-Doting, (ed.), Plenum Press, New York; Huttner, S. L., et al., 1992, Revising Oversight of Genetically Modified Plants, *Bio/Technology*; Klee, H., et al., 1989, Plant Gene Vectors and Genetic Transformation: Plant Transformation Systems Based on the use of *Agrobacterium tumefaciens, Cell Culture and Somatic Cell Genetics of Plants*; Koncz, C., et al., 1986, The Promoter of $T_L$-DNA Gene 5 Controls the Tissue-Specific Expression of Chimeric Genes Carried by a Novel Type of *Agrobacterium* Binary Vector; *Molecular and General Genetics*; Lawson, C., et al., 1990, Engineering Resistance to Mixed Virus Infection in a Commercial Potato Cultivar: Resistance to Potato Virus X and Potato Virus Y in Transgenic Russet Burbank, *Bio/Technology*; Mitsky, T. A., et al., 1996, Plants Resistant to Infection by PLRV. U.S. Pat. No. 5,510,253; Newell, C. A., et al., 1991, *Agrobacterium*-Mediated Transformation of *Solanum tuberosum* L. Cv. Russet Burbank, *Plant Cell Reports*; Perlak, F. J., et al., 1993, Genetically Improved Potatoes: Protection from Damage by Colorado Potato Beetles, *Plant Molecular Biology*; all of which are incorporated herein by reference for this purpose.

Many traits have been identified that are not regularly selected for in the development of a new variety but that can be improved by backcrossing and genetic engineering techniques. These traits may or may not be transgenic; examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these traits are described in U.S. Pat. No. 5,500,365, U.S. Pat. No. 5,387,756, U.S. Pat. No. 5,789,657, U.S. Pat. No. 5,503,999, U.S. Pat. No. 5,589,612, U.S. Pat. No. 5,510,253, U.S. Pat. No. 5,304,730, U.S. Pat. No. 5,382,429, U.S. Pat. No. 5,503,999, U.S. Pat. No. 5,648,249, U.S. Pat. No. 5,312,912, U.S. Pat. No. 5,498,533, U.S. Pat. No. 5,276,268, U.S. Pat. No. 4,900,676, U.S. Pat. No. 5,633,434 and U.S. Pat. No. 4,970,168.

Deposit Information

A tuber deposit of the J.R. Simplot Company proprietary POTATO CULTIVAR W8 disclosed above and recited in the appended claims has been made with the American Type Culture Collection (ATCC), 10801 University Boulevard, Manassas, Va. 20110. The date of deposit was Mar. 11, 2014. The deposit of 25 vials of microtubers was taken from the same deposit maintained by J.R. Simplot Company since prior to the filing date of this application. All restrictions will be irrevocably removed upon granting of a patent, and the deposit is intended to meet all of the requirements of 37 C.F.R. §§1.801-1.809. The ATCC Accession Number is PTA-121079. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A potato tuber, or a part of a tuber, of potato cultivar W8, wherein a representative sample of said tuber was deposited under ATCC Accession No. PTA-121079.

2. A potato plant, or a part thereof, produced by growing the tuber, or a part of the tuber, of claim 1.

3. A potato plant having all of the physiological and morphological characteristics of the plant of claim 2, and comprising the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

4. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flowers, stem and tuber, and wherein said tissue cultured cells comprise the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

5. A potato plant regenerated from the tissue culture of claim 4, wherein said plant has all of the physiological and morphological characteristics of potato cultivar W8.

6. A potato seed produced by growing the potato tuber, or a part of the tuber, of claim 1, wherein said seed comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

7. A potato plant, or a part thereof, produced by growing the seed of claim 6.

8. A potato plant regenerated from tissue culture of the potato plant of claim 7, wherein said regenerated plant comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

9. A method for producing a potato seed, said method comprising crossing two potato plants and harvesting the resultant potato seed, wherein at least one potato plant is the potato plant of claim 2.

10. A method for producing a potato seed, said method comprising crossing two potato plants and harvesting the resultant potato seed, wherein at least one potato plant is the potato plant of claim 7.

11. A potato seed produced by the method of claim 10, wherein said seed comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

12. A potato plant, or a part thereof, produced by growing said potato seed of claim 11.

13. A potato seed produced from the plant of claim 12, wherein said seed comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

14. The method of claim 9, wherein one of said potato plants is potato cultivar W8 and the second potato plant is transgenic.

15. A method of producing a potato seed, said method comprising crossing two potato plants and harvesting the resultant potato seed, wherein one of said potato plants is the potato plant of claim 7 and the second potato plant is transgenic.

16. A potato plant, or a part thereof, produced by growing the seed produced by the method of claim 14, wherein said plant comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

17. A method of introducing a desired trait into potato cultivar W8, wherein the method comprises:
（a）crossing a W8 plant, wherein a representative sample of tubers was deposited under ATCC Accession No. PTA-121079, with a plant of another potato cultivar that comprises a desired trait to produce progeny plants, wherein the desired trait is selected from the group consisting of male sterility, herbicide resistance, insect resistance, modified fatty acid metabolism, modified carbohydrate metabolism and resistance to bacterial disease, fungal disease or viral disease;
（b）selecting one or more progeny plants that have the desired trait;
（c）backcrossing the selected progeny plants with W8 plants to produce backcross progeny plants;
（d）selecting for backcross progeny plants that have the desired trait; and
（e）repeating steps (c) and (d) two or more times in succession to produce selected third or higher backcross progeny plants that comprise the desired trait.

18. A potato plant produced by the method of claim 17, wherein the plant has the desired trait and comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

19. The potato plant of claim 18, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

20. The potato plant of claim 18, wherein the desired trait is insect resistance and the insect resistance is conferred by a transgene encoding a *Bacillus thuringiensis* endotoxin.

21. The potato plant of claim 18, wherein the desired trait is modified fatty acid metabolism or modified carbohydrate metabolism and said desired trait is conferred by a nucleic acid encoding a protein selected from the group consisting of fructosyltransferase, levansucrase, α-amylase, invertase and starch branching enzyme or DNA encoding an antisense of stearyl-ACP desaturase.

22. A method of producing a commodity plant product, comprising obtaining the plant of claim 2, or a part thereof, and producing the commodity plant product from said plant or plant part thereof, wherein said commodity plant product is selected from the group consisting of French fries, potato chips, dehydrated potato material, potato flakes and potato granules.

23. The commodity plant product produced by the method of claim 22, wherein said product comprises the insert region of pSIM1278 that is present in cultivar W8 which contains inverted repeats of potato DNA effective for inhibition of expression of the endogenous asparagine synthetase-1 gene and the endogenous polyphenol oxidase-5 gene in addition to inverted repeats of the endogenous potato promoters for the phosphorylase-L and dikinase R1 genes and further comprising the insert region of pSIM1678 that is present in W8 which contains the potato late blight resistance gene Rpi-vnt1 and inverted repeats of potato DNA effective for inhibition of expression of the endogenous vacuolar invertase gene VInv.

\* \* \* \* \*